(12) United States Patent
Prabhakaran

(10) Patent No.: US 8,563,686 B2
(45) Date of Patent: Oct. 22, 2013

(54) CONFORMATIONALLY CONSTRAINED PEPTIDE MIMETICS

(75) Inventor: Erode N. Prabhakaran, Bangalore, IN (US)

(73) Assignee: Indian Institute of Science, Bangalore, Karnataka (IN)

( * ) Notice: Subject to any disclaimer, the term of this patent is extended or adjusted under 35 U.S.C. 154(b) by 501 days.

(21) Appl. No.: 12/551,101

(22) Filed: Aug. 31, 2009

(65) Prior Publication Data

US 2010/0261871 A1    Oct. 14, 2010

(30) Foreign Application Priority Data

Apr. 14, 2009    (IN) .............................. 850/CHE/2009

(51) Int. Cl.
*C07K 5/00* (2006.01)
(52) U.S. Cl.
USPC ........................................... 530/317; 514/34
(58) Field of Classification Search
USPC ......................................................... 530/317
See application file for complete search history.

(56) References Cited

U.S. PATENT DOCUMENTS 4,703,034 A * 10/1987 Freidinger et al. ............. 514/6.8
7,202,332 B2    4/2007 Arora et al.

OTHER PUBLICATIONS

Matsumoto et. al. Novel synthesis of alpha-amino carboxamides and their related compounds via alpha-oxo sulfones starting from 2,2 disulfoxiranes, Bulletin of the Chemical Society of Japan, 77(10), 1897-1903, 2004).*
Matsumoto et. al. Novel synthesis of alpha-amino carboxamides and their related compounds via alpha-oxo sulfones starting from 2,2 disulfoxiranes, Bulletin of the Chemical Society of Japan, 77(10), 1897-1903, 2004.*
Matsumoto et al., Bulletin of the Chemical Society of Japan, 77(1), 1897-1903, 2004).*
Basséne, C. E. et al., "Studies towards the conception of new selective PPARβIδ ligands," *Bioorganic and Medicinal Chemistry Letters*, 16:4528-4532 (2006).
Baumeister, R. et al., "Contacts between Tet Repressor and *tet* Operator Revealed by New Recognition Specificities of Single Amino Acid Replacement Mutants," *Journal of Molecular Biology*, 226(4):1257-1270 (1999).
Bigott-Hennkens, H. et al., "Synthesis and in Vitro Evaluation of a Rhenium-Cyclized Somatostatin Derivative Series," *Journal of Medicinal Chemistry*, 51(5):1223-1230 (2008).
Bisang, C. et al., "Synthesis, Conformational Properties, and Immunogenicity of a Cyclic Template-Bound Peptide Mimetic Containing and NPNA Motif from the Circumsporozoite Protein of *Plasmodium falciparum*," *Journal of the American Chemical Society*, 120:7439-7449 (1998).
Bisseger, P. et al., "Solid-phase synthesis of cyclic polyamines," *Tetrahedron*, 64(32):7531-7536 (2008).
Bouffard, J. et al., "A Highly Selective Fluorescent Probe for Thiol Bioimaging," *Organic Letters*, 10(1):37-40 (2008).
Brickmann, K. et al., "Synthesis of Conformationally Restricted Mimetics of γ-Turns and Incorporation into Desmopressin, an Analogue of the Peptide Hormone Vasopressin," *Chemistry-A European Journal*, 5(8):2241-2253 (1999).
Buil, M. et al., "Preparation of Half-Sandwich Alkyl-Titanium(IV) Complexes Stabilized by a Cyclopentadienyl Ligand with a Pendant Phosphine Tether and Their Use in the Catalytic Hydroamination of Aliphatic and Aromatic Alkynes," *Organometallics*, 25(17):4079-4089 (2006).
But, T. et al., "The Mitsunobu Reaction: Origin, Mechanism, Improvements, and Applications," *Chemistry-An Asian Journal*, 2:1340-1355 (2007).
Chae, J. et al., "Palladium-Catalyzed Regioselective Hydrodebromination of Dibromoindoles: Application to the Enantioselective Synthesis of Indolodioxane U86192A," *Journal of Organic Chemistry*, 69(10):3336-3339 (2004).
Chapman, R. et al., "A Highly Stable Short α-Helix Constrained by a Main-Chain Hydrogen-Bond Surrogate," *Journal of the American Chemistry Society*, 126:12252-12253 (2004).
Cluzeau, J. et al., "Design and synthesis of all diastereomers of cyclic pseudo-dipeptides as mimics of cyclic CXCR4 pentapeptide antagonists," *Organic and Biomolecular Chemistry*, 5(12):1915-1923 (2007).
Ferrer, C. et al., "Intra- and Intermolecular Reactions of Indoles with Alkynes Catalyzed by Gold," *Chemistry-A European Journal*, 13(5):1358-1373 (2007).
Fukumoto, Y. et al., "Anti-Markovnikov Addition of Both Primary and Secondary Amines to Terminal Alkynes Catalyzed by the $TpRh(C_2H_4)_2/PPh_3$ System," *Journal of the American Chemistry Society*, 129(45):13792-13793 (2007).
Garcia, J. et al., "Stabilization of the Biological Active Conformation of the Principal Neutralizing Determination of HIV-$1_{IIIB}$ Containing a *cis*-Proline Surrogate: $^1$H NMR and Molecular Modeling Study," *Biochemistry*, 45(13):4284-4294 (2006).
Gardner, R. A. et al., "Total Synthesis of Petrobactin and Its Homologues as Potential Growth Stimuli for *Marinobacter hydrocarbonoclasticus*, an Oil-Degrading Bacteria," *Journal of Organic Chemistry*, 69(10):3530-3537 (2004).
Gilon, C. et al., "A Backbone-Cyclic, Receptor 5-Selective Somatostatin Analogue: Synthesis, Bioactivity, and Nuclear Magnetic Resonance Conformational Analysis," *Journal of Medicinal Chemistry*, 41:919-929 (1998).
Graminski, G. et al., "A Rapid Bioassay for Platelet-Derived Growth Factor β-Receptor Tyrosine Kinase Function," *Nature Biotechnology*, 12:1008-1011 (1994).
Grigg, R. et al., "Kinetic acidity of iminium ions. 2-Alkynyl- and 2,5-dialkynyl-pyrrolidines via the iminium ion route to azomethine ylides," *Tetrahedron*, 58:2627-2640 (2002).

(Continued)

Primary Examiner — Cecilia J Tsang
Assistant Examiner — Jeanette Lieb
(74) Attorney, Agent, or Firm — Foley & Lardner LLP

(57) ABSTRACT

Conformationally constrained peptide mimetics in which a hydrogen bond interaction is replaced with a covalent hydrogen bond mimic are provided. Also provided are various methods of making these peptide mimetics.

13 Claims, No Drawings

(56) References Cited

OTHER PUBLICATIONS

Guisado, C. et al., "The facile preparation of primary and secondary amines via an improved Fukuyama-Mitsunobu procedure. Application to the synthesis of a lung-targeted gene delivery agent," *Organic and Biomolecular Chemistry*, 3:1049-1057 (2005).

Hadley, M., "Discovery that a melanocortin regulates sexual functions in male and female humans," *Peptides*, 26(10):1687-1689 (2005).

He, Y. et al., "Probing *met*repressor—operator recognition in solution," *Nature*, 359(6394):431-433 (1992).

Hocart, S. et al., "Potent Antagonists of Somatostatin: Synthesis and Biology," *Journal of Medicinal Chemistry*, 41:1146-1154 (1998).

Jelokhani-Niaraki, M. et al., "Interaction of Gramicidin S and its Aromatic Amino-Acid Analog with Phospholipid Membranes," *Biophysical Journal*, 95(7):3306-3321 (2008).

Kan, T. et al., "Ns strategies: a highly versatile synthetic method for amines," *Chemical Communications*, 353-359 (2004).

Kolomiets E. et al., "Structure and Properties of Supramolecular Polymers Generated from Heterocomplementary Monomers Linked through Sextuple Hydrogen-Bonding Arrays," *Macromolecules*, 39:1173-1181 (2006).

Lam, K. et al., "A new type of synthetic peptide library for identifying ligand-binding activity," *Nature*, 354:82-84 (1991).

Lambers, M. et al., "Highly Selective Hydroformylation of the Cinchona Alkaloids," *Journal of Organic Chemistry*, 67(14):5022-5024 (2002).

Le Bourdonnec, B. et al., "Discovery of a series of aminopiperidines as novel iNOS inhibitors," *Bioorganic and Medicinal Chemistry Letters*, 18:336-343 (2008).

Lehmler, H. et al., "Synthesis and structure of environmentally relevant perfluorinated sulfonamides," *Journal of Fluorine Chemistry*, 128:595-607 (2007).

Leigh, D. et al., "An ammonium/bis-ammonium switchable molecular shuttle," *Tetrahedron*, 64(36):8411-8416 (2008).

Lin, X. et al., "Utilization of Fukuyama's sulfonamide protecting group for the synthesis of N-substituted α-amino acids and derivatives," *Tetrahedron Letters*, 41:3309-3313 (2000).

Liu, S. et al., "Nonpeptide Somatostatin Agonists with $sst_4$ Selectivity: Synthesis and Structure-Activity Relationshops of Thioureas," *Journal of Medicinal Chemistry*, 41:4693-4705 (1998).

Mattern, R. et al., "Conformational Analyses of Somatostatin-Related Cyclic Hexapeptides Containing Peptoid Residues," *Journal of Medicinal Chemistry*, 41:2686-2692 (1998).

McKennon, M. et al., "A Convenient Reduction of Amino Acids and Their Derivatives," *Journal of Organic Chemistry*, 58:3568-3571 (1993).

Minin, P. et al., "Radical Ring Closures of 4-Isocyanato Carbon-Centered Radicals," *Journal of Organic Chemistry*, 68(7):2960-2963 (2003).

Moore, S. et al., "Discovery of Iodinated Somatostatin Analogues Selective for hsst2 and hsst5 with Excellent Inhibition of Growth Hormone and Prolactin Release from Rat Pituitary Cells," *Journal of Medicinal Chemistry*, 48(21):6643-6652 (2005).

Olsen, C. et al., "Fukuyama—Mitsunobu alkylation in amine synthesis on solid phase revisited: N-alkylation with secondary alcohols and synthesis of curtatoxins," *Tetrahedron*, 61:6046-6055 (2005).

Olsen, C. et al., "Aminolysis of Resin-Bound N-Nosylaziridine-2-carboxylic Acids," *Organic Letters*, 8(15):3371-3374 (2006).

Ordóñez, M. et al., "Highly diastereoselective synthesis of *anti*-γ-N-benzylamino-β-hydroxyphosphonates," *Chemical Communications*, 672-673 (2004).

Patino, N. et al., "Modelling, synthesis and biological evaluation of an ethidium—arginine conjugate linked to a ribonuclease mimic directed against TAR RNA of HIV-1," *European Journal of Medicinal Chemistry*, 37(7):573-584 (2002).

Ranu, B. et al., "Reduction of Imines with Zinc Borohydride Supported on Silica Gel. Highly Stereoselective Synthesis of Substituted Cyclohexylamines," *Journal of Organic Chemistry*, 62(6):1841-1842 (1997).

Rew, Y. et al., "Solid-Phase Synthesis of Amine-Bridged Cyclic Enkephalin Analogues via On-Resin Cyclization Utilizing the Fukuyama-Mitsunobu Reaction," *Journal of Organic Chemistry*, 67:8820-8826 (2002).

Sakamoto, I. et al., "Preparation of (Cyanomethylene)tributylphosphorane: A New Mitsunobu-Type Reagent," *Chemical & Pharmaceutical Bulletin*, 53(11):1508-1509 (2005).

Singh, Y. et al., "Structural Mimicry of Two Cytochrome $b_{562}$ Interhelical Loops Using Macrocycles Constrained by Oxazoles and Thiazoles," *Journal of the American Chemical Society*, 127(18):6563-6572 (2005).

Sohma, Y. et al., "Development of O-Acyl Isopeptide Method," *Peptide Science*, 88(2):253-262 (2007).

Somers, W. et al., "Crystal structure of the *met* repressor—operator complex at 2.8 Å resolution reveals DNA recognition by β-strands," *Nature*, 359(6394):387-393 (1992).

Tamaki, M. et al., "A Novel, Antimicrobially Active Analog of Gramicidin S without Amphiphilic Conformation," *Journal of Antibiotics*, 59(6):370-372 (2006).

Thayumanavan, R. et al., "Direct Organocatalytic Asymmetric Aldol Reactions of α-Amino Aldehydes: Expedient Syntheses of Highly Enantiomerically Enriched *anti*-β-Hydroxy-α-amino Acids," *Organic Letters*, 6(20):3541-3544 (2004).

Timofeeva, O. et al., "Rationally Designed Inhibitors Identify STAT3 N-Domain as a Promising Anticancer Drug Target," *ACS Chemical Biology*, 2(12):799-809 (2007).

Tran, T. et al., "Design, Synthesis, and Biological Activities of Potent and Selective Somatostatin Analogues Incorporating Novel Peptoid Residues," *Journal of Medicinal Chemistry*, 41:2679-2685 (1998).

Van Horn, B. et al., "Toward Cross-Linked Degradable Polyester Materials: Investigations into the Compatibility and Use of Reductive Amination Chemistry for Cross-Linking," *Macromolecules*, 40(5):1480-1488 (2007).

Williams, G. et al., "A One-Pot Process for the Enantioselective Synthesis of Amines via Reductive Amination under Transfer Hydrogenation Conditions," *Organic Letters*, 5(22):4227-4230 (2003).

Wohlrab, A. et al., "Total Synthesis of Plusbacin $A_3$: A Depsipeptide Antibiotic Active Against Vancomycin-Resistant Bacteria," *Journal of the American Chemical Society*, 129(14):4175-4177 (2007).

Yang, L. et al., "Spiro[1H-indene-1,4'-piperidine] Derivatives as Potent and Selective Non-Peptide Human Somatostatin Receptor Subtype 2 ($sst_2$) Agonists," *Journal of Medicinal Chemistry*, 41(13):2175-2179 (1998).

Ying, J. et al., "Design, Synthesis, and Biological Evaluation of New Cyclic Melanotropin Peptide Analogues Selective for the Human Melanocortin-4 Receptor," *Journal of Medicinal Chemistry*, 49(23):6888-6896 (2006).

Zapf, C. et al., "Utilizing the intramolecular Fukuyama—Mitsunobu reaction for a flexible synthesis of novel heterocyclic scaffolds for peptidomimetic drug design," *Bioorganic and Medicinal Chemistry Letters*, 15:4033-4036 (2005).

Basak, A., and Kar, M., "Benzofused N-substituted cyclic enediynes: activation and DNA-cleavage potential," Bioorganic and Medicinal Chemistry, vol. 16, Issue: 8, pp. 4532-4537 (2008).

Nagy, A., "Synthesis and biological evaluation of cytotoxic analogs of somatostatin containing doxorubicin or its intensely potent derivative,0092-pyrrolinodoxorubicin," Proceedings of the National Academy of Sciences of the United States of America, vol. 95, No. 4, pp. 1794-1799, The National Academy of Sciences (1998).

Yang, L., et al., "Synthesis and biological activities of potent peptidomimetics selective for somatostatin receptor subtype 2," Proceedings of the National Academy of Sciences of the United States of America, vol. 95, No. 18, pp. 18836-10841, The National Academy of Sciences (1998).

* cited by examiner

CONFORMATIONALLY CONSTRAINED PEPTIDE MIMETICS

BACKGROUND OF THE TECHNOLOGY

Due to their essential role in the regulation of all physiological metabolic pathways, proteins can be useful drugs (as both agonists and/or antagonists) for the treatment of a variety of physiological disorders or diseases. The biological activity of proteins is often mediated by the distinct conformations that they exist in or are able to access. Thus, for example, proteins exhibit structural motifs, known as secondary structure, which include various turn (e.g. gamma- and beta-turns), sheet (beta sheet) and helical (alpha helix and pi helix) conformations. However, limitations in the size of molecules allowed into cells through naturally occurring non-invasive transduction pathways (e.g. endocytosis) generally limits or precludes the use of whole proteins as drugs. Consequently, short peptide sequences containing the functional domain(s) of the whole protein are preferred drug candidates.

Proteins can also be the targets of small molecule drugs. Designing small molecule drugs often involves assaying the activity of the drug candidates against shorter peptide sequences containing the functional domain(s) of the whole protein target. In both cases, because short peptide sequences often lack sufficient binding interactions (e.g., hydrogen bonding interactions, solvophobic interactions, electrostatic interactions, disulphide bonds, etc.), they are unable to access the same native, folded conformations when removed from the whole protein, thereby limiting their usefulness as drugs or drug targets.

SUMMARY OF THE TECHNOLOGY

Provided herein are novel compounds which constrain peptides in order to mimic their natural biologically active conformations. In compounds disclosed herein, one or more hydrogen bonds (e.g., 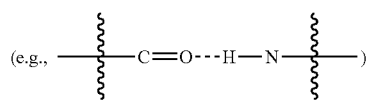 )

are replaced with a covalent hydrogen bond mimic or linker, (e.g., 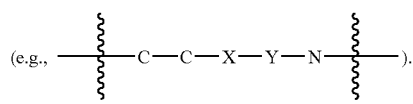 ).

Amino-acid containing compounds including such hydrogen bond mimics are capable of mimicking a variety of a secondary peptide structures, including γ-turns, β-turns, α-helices, and π-helices as well as tertiary peptide structures. Further, the side-chains on the covalent linker assist in providing secondary interactions between different secondary structures, aid molecular recognition, act as additional structure constraining elements and influence the topological variations on the peptide surface. The compounds are useful as synthetic peptide drugs and as model targets for the design of small molecule drugs. Thus, the compounds disclosed herein are capable of mimicking the utility of the corresponding biologically active peptides and proteins from which they are designed. Various methods of preparing the compounds are also provided. These methods allow both intra- and intermolecular links between peptides and allow peptidic or non-peptidic extensions at all termini of the constrained peptide mimetic while retaining all the native amino acid side-chains in the sequence. Also provided are compositions including the compounds.

The foregoing summary is illustrative only and is not intended to be in any way limiting. In addition to the illustrative aspects, embodiments, and features described above, further aspects, embodiments, and features will become apparent by reference to the following detailed description.

DETAILED DESCRIPTION OF THE TECHNOLOGY

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

The following terms are used throughout as described below, unless context clearly indicates otherwise.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the technology. Procedures for inserting such labels into the compounds of the technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like. Substituted also includes multiple substitution e.g., disubstituted groups such as dialkyl, diaryl etc.

Substituted ring groups such as substituted cycloalkyl, aryl, heterocyclyl and heteroaryl groups also include rings and fused ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms, and typically from 1 to 10 carbons or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, carboxyalkyl, and the like.

Cycloalkyl groups include mono-, bi- or tricyclic alkyl groups having from 3 to 14 carbon atoms in the ring(s), or, in some embodiments, 3 to 12, 3 to 10, 3 to 8, or 3, 4, 5, or 6 carbon atoms. Illustrative monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups such as, but not limited to, adamantyl, and fused rings, such as, but not limited to, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4-2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Thus, alkenyl groups have from 2 to 12 carbon atoms, and typically from 2 to 10 carbons or, in some embodiments, from 2 to 8, 2 to 6, or 2 to 4 carbon atoms. Examples include, but are not limited to vinyl, allyl, —CH═CH(CH$_3$), —CH═C(CH$_3$)$_2$, —C(CH$_3$)═CH$_2$, —C(CH$_3$)═CH(CH$_3$), —C(CH$_2$CH$_3$)═CH$_2$, among others. Representative substituted alkenyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, that may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 12 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass partially unsaturated and saturated ring systems, such as, for example, imidazolinyl and imidazolidinyl groups. The phrase "heterocyclyl group" includes fused ring species, including for example, hexahydropyrrolizine. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups". Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, pyrrolinyl, imidazolyl, imidazolinyl, pyrazolinyl, thiazolinyl, piperidyl, piperazinyl, morpholinyl, thiomorpholinyl, tetrahydropyranyl, tetrahydrothiopyranyl, oxathiane, dithianyl, pyranyl, dihydropyridyl, dihydrodithiinyl, dihydrodithionyl, homopiperazinyl, quinuclidyl, indolinyl, indolizinyl, benzoxazinyl, benzodithiinyl, benzoxathiinyl, benzothiazinyl, benzoxazolyl, benzothiazolyl, benzothiadiazolyl, benzo[1,3]dioxolyl, quinolizinyl, quinoxalinyl, quinazolinyl, cinnolinyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, piperazin-1-yl-methyl, tetrahydrofuran-2-yl-ethyl, and piperidinyl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the technology are not referred to using the "ene" designation. Thus, e.g., chloroethyl is not referred to herein as chloroethylene.

Alkoxy and cycloalkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The terms "carboxyl" and "carboxy" as used herein refers to a —COOH group.

The term "ester" as used herein refers to —COOR$^{30}$ groups. R$^{30}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{31}$R$^{32}$, and —NR$^{31}$C(O)R$^{32}$ groups, respectively. R$^{31}$ and R$^{32}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H).

Urethane groups include N- and O-urethane groups, i.e., —NR$^{33}$C(O)OR$^{34}$ and —OC(O)NR$^{33}$R$^{34}$ groups, respectively. R$^{33}$ and R$^{34}$ are independently a substituted or unsubstituted alkyl, alkenyl, alkynyl, cycloalkyl, aryl, aralkyl, heterocyclylalkyl, or heterocyclyl group as defined herein. R$^{33}$ may also be —H.

The term "amine" (or "amino") as used herein refers to —NHR$^{35}$ and —NR$^{36}$R$^{37}$ groups, wherein R$^{35}$, R$^{36}$ and R$^{37}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{38}$R$^{39}$ and —NR$^{38}$SO$_2$R$^{39}$ groups, respectively. R$^{38}$ and R$^{39}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$).

The term "thiol" refers to —SH groups, while sulfides include —SR$^{40}$ groups, sulfoxides include —S(O)R$^{41}$ groups, sulfones include —SO$_2$R$^{42}$ groups, and sulfonyls include —SO$_2$OR$^{43}$. R$^{40}$, R$^{41}$, R$^{42}$ and R$^{43}$ are each independently a substituted or unsubstituted alkyl, cycloalkyl, alkenyl, alkynyl, aryl aralkyl, heterocyclyl or heterocyclylalkyl group as defined herein.

The term "urea" refers to —NR$^{44}$—C(O)—NR$^{45}$R$^{46}$ groups. R$^{44}$, R$^{45}$, and R$^{46}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{47}$)NR$^{48}$R$^{49}$ and —NR$^{47}$C(NR$^{48}$)R$^{49}$, wherein R$^{47}$, R$^{48}$, and R$^{49}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{50}$C(NR$^{51}$)NR$^{52}$R$^{53}$, wherein R$^{50}$, R$^{51}$, R$^{52}$ and R$^{53}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{54}$)=C(R$^{55}$)NR$^{56}$R$^{57}$ and —NR$^{54}$C(R$^{55}$)=C(R$^{56}$)R$^{57}$, and wherein R$^{54}$, R$^{55}$, R$^{56}$ and R$^{57}$ are each independently hydrogen, a substituted or unsubstituted alkyl, cycloalkyl, alkenyl, alkynyl, aryl aralkyl, heterocyclyl or heterocyclylalkyl group as defined herein.

The term "imide" refers to —C(O)NR$^{58}$C(O)R$^{59}$, wherein R$^{58}$ and R$^{59}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{60}$(NR$^{61}$) and —N(CR$^{60}$R$^{61}$) groups, wherein R$^{60}$ and R$^{61}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{60}$ and R$^{61}$ are not both simultaneously hydrogen.

The term "leaving group" refers to an atom or group of atoms which may be replaced by another atom or group of atoms (e.g., a nucleophile, such as an amine, thiol, carbanion, and the like) during a chemical reaction. Illustrative leaving groups are well known in the art and include, but are not limited to halogen groups (e.g., I, Br, F, Cl), sulfonate groups (e.g., mesylate, tosylate, triflate), substituted alkylsulfonate groups (e.g., haloalkylsulfonate); C$_6$-aryloxy or substituted C$_6$-aryloxy groups; acyloxy groups and the like.

The term "protected" with respect to hydroxyl groups, amine groups, carboxy groups, and thiol groups refers to forms of these functionalities that are protected from undesirable reaction by means of protecting groups. Protecting groups such as hydroxyl, amino, carboxy, and thiol protecting groups, are known to those skilled in the art and can be added or removed using well-known procedures such as those set forth in Protective Groups in Organic Synthesis, Greene, T. W.; Wuts, P. G. M., John Wiley & Sons, New York, N.Y., (3rd Edition, 1999). Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylhiomethyl ether, benzyloxymethyl ether, t-butoxymethyl ether, 2-methoxyethoxymethyl ether, tetrahydropyranyl ethers, 1-ethoxyethyl ether, t-butyl ether, allyl ether, benzyl ether; esters such as, but not limited to, benzoyl, formate, acetate, trichloroacetate, and trifluoracetate.

Amino-Protecting groups (also known as N-protecting groups) comprise acyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, a-chlorobutyryl, benzoyl, 4-chlorobenzoyl, 4-bromobenzoyl, 4-nitrobenzoyl, and the like; sulfonyl groups such as benzenesulfonyl, p-toluenesulfonyl and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxycarbonyl, fluorenyl-9-methoxycarbonyl, cyclopentyloxycarbonyl, adamantyloxycarbonyl, cyclohexyloxycarbonyl, phenylthiocarbonyl and the like; alkyl groups such as benzyl, triphenylmethyl, benzyloxymethyl and the like; and silyl groups such as trimethylsilyl and the like. Typical amino-protecting groups include formyl, acetyl, benzoyl, pivaloyl, t-butylacetyl, phenylsulfonyl, benzyl, 9-fluorenylmethyloxycarbonyl (Fmoc), t-butyloxycarbonyl (Boc) and benzyloxycarbonyl (Cbz).

Examples of protected thiol groups include, but are not limited to, thioethers such as S-benzyl thioether, S-t-butylthioether, and S-4-picolyl thioether; substituted S-methyl derivatives such as hemithio, dithio and aminothio acetals; and others.

Representative carboxy protecting groups are C$_1$ to C$_8$ alkyl (e.g., methyl, ethyl or tertiary butyl and the like); haloalkyl, such as trichloryphtye and the like; alkenyl, such as allyl and the like; cycloalkyl and substituted derivatives thereof such as cyclohexyl, cyclopentyl and the like; cycloalkylalkyl and substituted derivatives thereof such as cyclohexylmethyl, cyclopentylmethyl and the like; arylalkyl, for example, phenethyl or benzyl and substituted derivatives thereof such as alkoxybenzyl or nitrobenzyl groups and the like; arylalkenyl, for example, phenylethenyl and the like; aryl and substituted derivatives thereof, for example, 5-indanyl and the like; dialkylaminoalkyl (e.g., dimethylaminoethyl and the like); alkanoyloxyalkyl groups such as acetoxymethyl, butyryloxymethyl, valeryloxymethyl, isobutyryloxymethyl, isovaleryloxymethyl, 1-(propionyloxy)-1-ethyl, 1-(pivaloyloxyl)-1-ethyl, 1-methyl-1-(propionyloxy)-1-ethyl, pivaloyloxymethyl, propionyloxymethyl and the like; cycloalkanoyloxyalkyl groups such as cyclopropylcarbonyloxymethyl, cyclobutylcarbonyloxymethyl, cyclopentylcarbonyloxymethyl, cyclohexylcarbonyloxymethyl and the like; aroyloxyalkyl, such as benzoyloxymethyl, benzoyloxyethyl and the like; arylalkylcarbonyloxyalkyl, such as benzylcarbonyloxymethyl, 2-benzylcarbonyloxyethyl and the like; alkoxycarbonylalkyl, such as methoxycarbonylmethyl, cyclohexyloxycarbonylmethyl, 1-methoxycarbonyl-1-ethyl, and the like; alkoxycarbonyloxyalkyl, such as methoxycarbonyloxymethyl, t-butyloxycarbonyloxymethyl, 1-ethoxycarbonyloxy-1-ethyl, 1-cyclohexyloxycarbonyloxy-1-ethyl and the like; alkoxycarbonylaminoalkyl, such as t-butyloxycarbonylaminomethyl and the like; alkylaminocarbonylaminoalkyl, such as methylaminocarbonylaminomethyl and the like; alkanoylaminoalkyl, such as acetylaminomethyl and the like; heterocyclylcarbonyloxyalkyl, such as 4-methylpiperazinylcarbonyloxymethyl and the like; dialkylaminocarbonylalkyl, such as dimethylaminocarbonylmethyl, diethylaminocarbonylmethyl and the like; (5-(alkyl)-2-oxo-1,3-dioxolen-4-yl)alkyl, such as (5-t-butyl-2-oxo-1,3-dioxolen-4-yl)methyl and the like; and (5-phenyl-2-oxo-1,3-dioxolen-4-yl)alkyl, such as (5-phenyl-2-oxo-1,3-dioxolen-4-yl) methyl and the like.

Those of skill in the art will appreciate that compounds of the technology may exhibit the phenomena of tautomerism, conformational isomerism, geometric isomerism and/or stereoisomerism. As the Formula drawings within the specification and claims can represent only one of the possible tautomeric, conformational isomeric, stereoisomeric or geometric isomeric forms, it should be understood that the technology encompasses any tautomeric, conformational isomeric, stereoisomeric and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, imidazoles may exhibit the following isomeric forms, which are referred to as tautomers of each other:

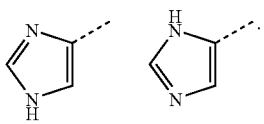

As readily understood by one skilled in the art, a wide variety of functional groups and other structures may exhibit tautomerism, and all tautomers of compounds as described herein are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the technology.

The compounds of the technology may exist as solvates, especially hydrates. Hydrates may form during manufacture of the compounds or compositions comprising the compounds, or hydrates may form over time due to the hygroscopic nature of the compounds. Compounds of the technology may exist as organic solvates as well, including DMF, ether, and alcohol solvates among others. The identification and preparation of any particular solvate is within the skill of the ordinary artisan of synthetic organic or medicinal chemistry.

Provided herein are novel conformationally constrained peptide mimetic compounds that are useful as peptide drugs or peptide drug targets. Thus, in accordance with one aspect, provided herein are compounds of Formula I:

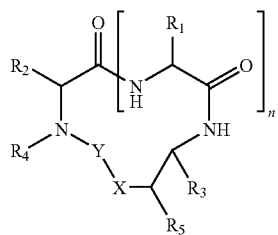

I wherein

X is —$CR_aR_b$—;

Y is —$CR_cR_d$—;

$R_a$, $R_b$, $R_c$, and $R_d$ are independently —H or a substituted or unsubstituted alkyl or aralkyl group;

$R_1$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl, or heteroaralkyl group; or, $R_1$ together with the carbon to which it is attached and the adjacent nitrogen, forms a substituted or unsubstituted pyrrolidine, oxazolidine, thiazolidine, imidazolidine, or piperidine ring;

$R_2$ and $R_3$ are independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group; or $R_2$ and $R_4$ together with the atoms to which they are attached form a substituted or unsubstituted pyrrolidine, oxazolidine, thiazolidine, imidazolidine, or piperidine ring;

$R_4$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, —C(O)—$R_1$, or a —C(O)—$CHR_1$—NH—$R_6$ group; or $R_4$ and $R_2$ together with the atoms to which they are attached form a substituted or unsubstituted pyrrolidine, oxazolidine, thiazolidine, imidazolidine, or piperidine ring;

$R_5$ is a —H, a substituted or unsubstituted alkyl, aryl, aralkyl, heteroaryl or a heteroaralkyl group, —$NH_2$, —NH—C(O)—$R_7$, or a —NH—$CHR_1$—C(O)—$R_7$ group;

$R_6$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, $C(O)R_{10}$, —[C(O)—$CHR_1$—NH]$_m$—$R_{10}$, —[C(O)—$CHR_1$—NH]$_m$—C(O)$R_{10}$, —[C(O)—$CHR_1$—NH]$_m$—C(O)$OR_{10}$;

$R_7$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, $NR_{10}R_{10}$, or —[NH—$CHR_1$—C(O)]$_m$—;

$R_{10}$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group;

m at each occurrence is independently an integer from 1 to 20; and n is an integer from 0 to 20.

In some embodiments of compounds of Formula I, $R_a$ is a substituted or unsubstituted $C_{1-6}$ alkyl group, $R_c$ is a substituted or unsubstituted $C_{1-6}$ alkyl group, or both $R_a$ and $R_c$ are substituted or unsubstituted $C_{1-6}$ alkyl groups. In other embodiments, $R_b$ is —H, $R_d$ is —H, or both $R_b$ and $R_d$ are —H.

In some embodiments of the compounds of Formula I, X is —$CH_2$—. In other embodiments, Y is —$CH_2$—. In yet other embodiments, each of X and Y is —$CH_2$—.

In certain embodiments of the compounds of Formula I, $R_1$ and $R_2$ are independently —H, benzyl optionally substituted with one or more OH or halogen, imidazolylmethyl, indolylmethyl, or a $C_{1-6}$ alkyl group optionally substituted with one or more substituents selected from —F, —Cl, —Br, —I, —OH, —O-$PG_1$, —SH, —S-$PG_2$, —$NH_2$, —NH-$PG_3$, —C(O)OH, —C(O)O-$PG_4$, —C(O)$NH_2$, or —NHC(NH)$NH_2$; wherein $PG_1$ is a hydroxyl protecting group, $PG_2$ is a thiol protecting group, $PG_3$ is an amino protecting group, and $PG_4$ is a carboxyl protecting group. In some embodiments, $R_1$ at each occurrence and $R_2$ are independently selected from the group consisting of —H, methyl, isopropyl, isobutyl, sec-butyl, hydroxymethyl, 1-hydroxyethyl, thiomethyl, 4-aminobutyl, 3-guanidinopropyl, benzyl, 4-hydroxybenzyl, indolylmethyl, methylthioethyl, carboxymethyl, carboxyethyl, carboxamidomethyl, carboxamidoethyl, and imidazolylmethyl. In some embodiments, $R_2$ is —H. In other embodiments, $R_3$ is —H. In still other embodiment, $R_2$ and $R_4$ together with the atoms to which they are attached form a substituted or unsubstituted pyrrolidine ring.

In some embodiments of the compounds of Formula I, $R_4$ is —H, $R_5$ is —H or both $R_4$ and $R_5$ are —H. In other embodiments, $R_4$ is a —$CHR_1$—NH—$R_6$ group. In some embodiments, $R_6$ is —H, —C(O)$R_{10}$, —C(O)$OR_{10}$, —[C(O)—$CHR_1$—NH]$_m$—$R_{10}$, or —[C(O)—$CHR_1$—NH]$_m$—C(O)$R_{10}$. In other embodiments, $R_5$ is a —$CHR_1$—C(O)—$R_7$ group. In some embodiments, $R_7$ is —$OR_{10}$, —$NR_{10}R_{10}$, or —[NH—$CHR_1$—C(O)]$_m$.

In some embodiments of the compounds of Formula I, n is 1, 2, or 3.

In another aspect, provided herein are a compounds of Formula II.

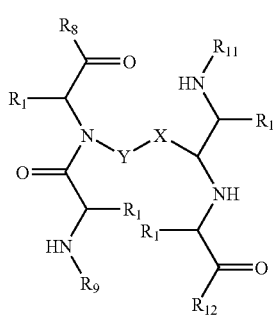

wherein
X is —CR$_a$R$_b$—;
Y is —CR$_c$R$_d$—;
R$_a$, R$_b$, R$_c$, and R$_d$ are independently —H or a substituted or unsubstituted alkyl or aralkyl group;
R$_1$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl, or heteroaralkyl group; or, R$_1$ together with the carbon to which it is attached and the adjacent nitrogen, forms a substituted or unsubstituted pyrrolidine, oxazolidine, thiazolidine, imidazolidine, or piperidine ring;
R$_8$ and R$_{12}$ are independently —OR$_{10}$, —NR$_{10}$R$_{10}$, —[NH—CHR$_1$—C(O)]$_m$—OR$_{10}$, or —[NH—CHR$_1$—C(O)]$_m$—NR$_{10}$R$_{10}$;
R$_9$ and R$_{11}$ are independently —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, —C(O)R$_{10}$, —[C(O)—CHR$_1$—NH]$_m$—R$_{10}$, —[C(O)—CHR$_1$—NH]$_m$—C(O)R$_{10}$, or —[C(O)—CHR$_1$—NH]$_m$—C(O)OR$_{10}$;
R$_{10}$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group; and
m at each occurrence is independently an integer from 1 to 20.

In some embodiments of the compounds of Formula II, R$_a$ is a substituted or unsubstituted C$_{1-6}$ alkyl group, R$_c$ is a substituted or unsubstituted C$_{1-6}$ alkyl group, or both R$_a$ and R$_c$ are substituted or unsubstituted C$_{1-6}$ alkyl groups. In other embodiments, R$_b$ is —H, R$_d$ is —H, or both R$_b$ and R$_d$ are —H.

In some embodiments of the compounds of Formula II, X is —CH$_2$—. In other embodiments, Y is —CH$_2$—. In yet other embodiments, each of X and Y is —CH$_2$—.

In certain embodiments of the compounds of Formula II, R$_1$ and R$_2$ are independently —H, benzyl optionally substituted with one or more OH or halogen, imidazolylmethyl, indolylmethyl, or a C$_{1-6}$ alkyl group optionally substituted with one or more substituents selected from —F, —Cl, —Br, —I, —OH, —O-PG$_1$, —SH, —S-PG$_2$, —NH$_2$, —NH-PG$_3$, —C(O)OH, —C(O)O-PG$_4$, —C(O)NH$_2$, or —NHC(NH)NH$_2$; wherein PG$_1$ is a hydroxyl protecting group, PG$_2$ is a thiol protecting group, PG$_3$ is an amino protecting group, and PG$_4$ is a carboxyl protecting group. In other embodiments, R$_1$ at each occurrence and R$_2$ are independently selected from the group consisting of —H, methyl, isopropyl, isobutyl, sec-butyl, hydroxymethyl, 1-hydroxyethyl, thiomethyl, 4-aminobutyl, 3-guanidinopropyl, benzyl, 4-hydroxybenzyl, indolylmethyl, methylthioethyl, carboxymethyl, carboxyethyl, carboxamidomethyl, carboxamidoethyl, and imidazolylmethyl.

In some embodiments of the compounds of Formula II, R$_8$ and R$_{12}$ are independently selected from —[NH—CHR$_1$—C(O)]$_m$—OR$_{10}$ or —[NH—CHR$_1$—C(O)]$_m$—NR$_{10}$R$_{10}$.

In some embodiments of the compounds of Formula II, R$_9$ and R$_{11}$ are independently selected from —[C(O)—CHR$_1$—NH]$_m$—R$_{10}$, —[C(O)—CHR$_1$—NH]$_m$—C(O)R$_{10}$, or —[C(O)—CHR$_1$—NH]$_m$—C(O)OR$_{10}$.

In some embodiments of the compounds of Formula II, m at each occurrence is independently an integer from 1 to 10.

In one aspect, there are provided a compounds of Formula III, IV, V, XIX and XX, useful as intermediates in the synthesis of compounds of Formula II or as mimetics themselves:

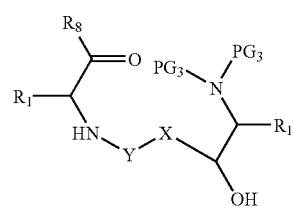

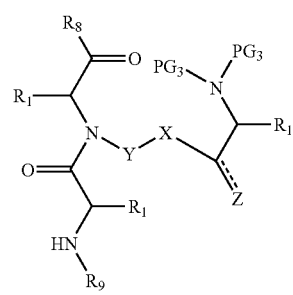

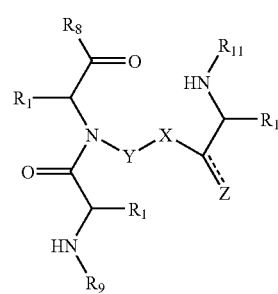

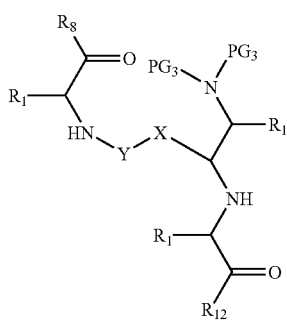

(XIX)

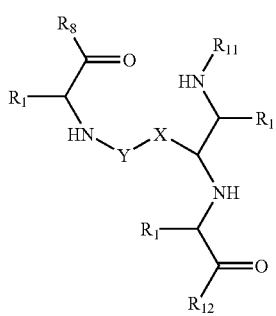

(XX)

wherein

X is —CR$_a$R$_b$—;

Y is —CR$_c$R$_d$—;

Z is —OH, a leaving group, a protected oxo group, or an unprotected oxo group, and the dashed line indicates a single bond when Z is —OH, a leaving group or a protected oxo group, or a double bond when Z is an oxo group;

R$_a$, R$_b$, R$_c$ and R$_d$ are independently —H or a substituted or unsubstituted alkyl or aralkyl group;

R$_1$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl, or heteroaralkyl group; or, R$_1$ together with the carbon to which it is attached and the adjacent nitrogen, forms a substituted or unsubstituted pyrrolidine, oxazolidine, thiazolidine, imidazolidine, or piperidine ring;

R$_8$ and R$_{12}$ are independently —OR$_{10}$, —NR$_{10}$R$_{10}$, —[NH—CHR$_1$—C(O)]$_m$—OR$_{10}$, or —[NH—CHR$_1$—C(O)]$_m$—NR$_{10}$R$_{10}$;

R$_9$ and R$_{11}$ are independently —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, —C(O)R$_{10}$, —[C(O)—CHR$_1$—NH]$_m$—R$_{10}$, —[C(O)—CHR$_1$—NH]$_m$—C(O)R$_{10}$, or —[C(O)—CHR$_1$—NH]$_m$—C(O)OR$_{10}$;

R$_{10}$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group;

PG$_3$ at each occurrence is independently an amino protecting group; or two PG$_3$ groups may represent a single divalent amino protecting group; and m at each occurrence is independently an integer from 1 to 20.

In some embodiments of the compounds of Formula III, IV, V, XIX and XX, the PG$_3$ groups together with the nitrogen to which they are attached form pthalimide. In other embodiments, each PG$_3$ group is independently selected from t-butyloxycarbonyl, benzyloxycarbonyl, or fluorenylmethyloxycarbonyl.

In certain embodiments of the compounds of Formula III, IV, V, XIX and XX, Z is —Cl, —Br, —I, mesylate, tosylate, triflate, or a protected or unprotected keto carbonyl group.

In some embodiments of the compounds of Formula III, IV, V, XIX and XX, R$_a$ is a substituted or unsubstituted C$_{1-6}$ alkyl group, R$_c$ is a substituted or unsubstituted C$_{1-6}$ alkyl group, or both R$_a$ and R$_c$ are substituted or unsubstituted C$_{1-6}$ alkyl groups. In some embodiments, R$_b$ is —H, R$_d$ is —H, or both R$_b$ and R$_d$ are —H.

In some embodiments of the compounds of Formula III, IV, V, XIX and XX, X is —CH$_2$—. In other embodiments, Y is —CH$_2$—. In yet other embodiments, each of X and Y is —CH$_2$—.

In certain embodiments of the compounds of Formula III, IV, V, XIX and XX, R$_1$ is independently —H, benzyl optionally substituted with one or more OH or halogen, imidazolylmethyl, indolylmethyl, or a C$_{1-6}$ alkyl group optionally substituted with one or more substituents selected from —F, —Cl, —Br, —I, —OH, —O-PG$_1$, —SH, —S-PG$_2$, —NH$_2$, —NH-PG$_3$, —C(O)OH, —C(O)O—PG$_4$, —C(O)NH$_2$, or —NHC(NH)NH$_2$; wherein PG$_1$ is a hydroxyl protecting group, PG$_2$ is a thiol protecting group, PG$_3$ is an amino protecting group, and PG$_4$ is a carboxyl protecting group.

In some embodiments of the compounds of Formula III, IV, V, XIX and XX, R$_8$ and R$_{12}$ are independently selected from —[NH—CHR$_1$—C(O)]$_m$—OR$_{10}$ or —[NH—CHR$_1$—C(O)]$_m$—NR$_{10}$R$_{10}$.

In some embodiments of the compounds of Formula III, IV, V, and XX, R$_9$ and R$_{11}$ are independently selected from —[C(O)—CHR$_1$—NH]$_m$—R$_{10}$, —[C(O)—CHR$_1$—NH]$_m$—C(O)R$_{10}$, or —[C(O)—CHR$_1$—NH]$_m$—C(O)OR$_{10}$.

In some embodiments of the compounds of Formula III, IV, V, XIX and XX, m at each occurrence is independently an integer from 1 to 10.

In another aspect, the disclosure provides methods of making the group of constrained peptide mimetic compounds of Formula I, II, III, IV, V, XIX and XX. These compounds may be synthesized by solution and solid phase synthesis methods. The following methods are offered by way of example and are not limiting. Those of skill in the art will understand that many similar methods may be used to produce compounds described herein.

As shown in Scheme 1, compounds of Formula I can be made by solution-phase methods employing standard protecting group strategies and coupling reagents. The variables depicted have the meanings set forth above for Formula I, and Z is a hydroxyl or a leaving group (e.g., Br, mesyl, tosyl, or another such group derived from hydroxyl). Details of each of the possible steps 1-5 are as follows.

Scheme 1

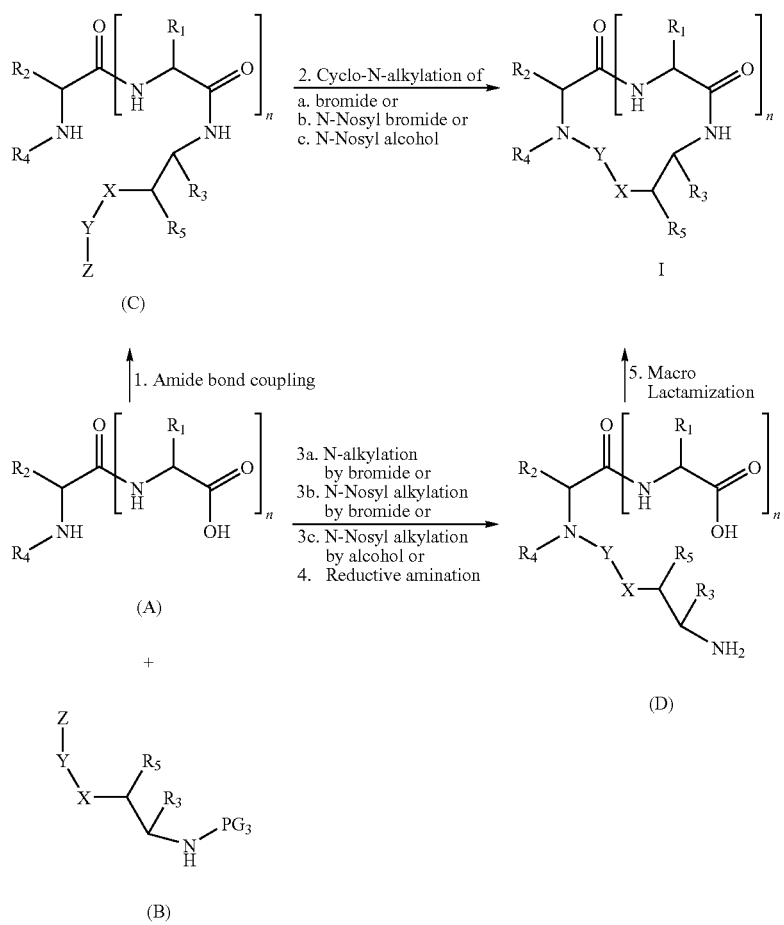

Step 1. Amide Bond Coupling Reaction

The amide bond coupling reaction between the carboxylic acid (A) and alkyl amine (B) shown in Scheme I can be conducted using standard methods known in the art. Prior to coupling, the N-protecting group (e.g., Boc or Fmoc) of compound (B) may be removed by standard procedures such as e.g., acidic or basic conditions. Alternatively, for amino bromides of the type (B) which are sensitive to basic conditions of the standard coupling protocol, the corresponding amino alcohol (Z=OH in (B)) can be used instead, for the peptide coupling (with A) and the resulting peptide alcohol can be converted to the corresponding bromide in the presence of a trialkyl phosphine such as $PPh_3$ and a Br source such as NBS or $CBr_4$. Coupling agents may be used, for example, in the presence of a base and a suitable solvent such as, e.g., HATU, TEA, and DMF as disclosed in *Org. Biomol. Chem.,* 2007, 1915-1923, or Bop, DIPEA, DCM, or Bop, HOBt, DIEA, DMF, or DCC, HOSu, DMF, NMM, as disclosed in *European Journal of Medicinal chemistry,* 2002, 37(7), 573-584. Standard N-protecting groups ($PG_3$) as disclosed herein may be used including, but are not limited to, Boc, Cbz and Fmoc.

Step 2a. Cyclo N-Alkylation of Peptidic Amino Bromides

When Z is a bromine and $R_4$ is not nosyl, compound (C) may be cyclized by treatment with an alkali metal carbonate such as $NaHCO_3$, $K_2CO_3$ or $Na_2CO_3$, in a suitable solvent such as, but not limited to, $H_2O$, MeOH, $CH_3CN$ or mixtures of any two or more thereof, at concentrations varying from 1-100 mM at temperatures ranging from about r.t. up to about 90° C.

Step 2b. Cyclo N-Alkylation of N-Nosyl Peptidic Alkyl Bromides

The cyclo-N-alkylation of compound (C) shown in Scheme I may be carried out by intramolecular N-alkylation of N-nosyl bromides as disclosed in *J. Am. Chem. Soc.* 2004, 126, 12252-12253. Thus, a dilute solution of the N-nosyl peptidic alkyl bromide in a suitable solvent such as DMF can be stirred with an alkali metal carbonate such as e.g. $K_2CO_3$ or $Na_2CO_3$ to obtain the compound of formula (I). Alternatively, the cyclo N-alkylation can be conducted according to the method disclosed in *Tetrahedron* 2008, 64(32), 7531-7536, wherein the N-nosyl peptidic alkyl bromide is dissolved in a suitable solvent such as DMF and reacted with $Cs_2CO_3$ to give a compound of formula I. As will be understood by the skilled artisan, with slight modification, the intermolecular solution phase reaction set forth in the following references may also be used for the present cyclization: *Chemistry A Eur. J.* 2007, 13(5), 1358-1373; and *Tetrahedron* 2008, 64(36), 8411-8416.

Step 2c. Cyclo N-Alkylation of N-Nosyl Peptidic Alcohols

The cyclo-N-alkylation of N-nosyl (or N-2,4-dinitrobenzene sulfonamide) alcohols can conducted using the Fukuyama Mitsunobu reaction, either in solution phase or on solid phase using activating reagents and a base such as $PPh_3$ (e.g., 3 eq.), DEAD (or DIAD) (e.g., 2 eq.), DIPEA (or TEA) (e.g., 3 eq.) in a solvent such as THF. The general process for this step is as disclosed in the following references: *Bioorganic & Medicinal Chemistry* 2008, 16, 4532-4537; *Tetrahedron* 2008, 64(32), 7531-7536; and *Bioorganic & Medicinal Chemistry Letters* 2008, 15, 4033-4036, which disclose the intramolecular solution phase Fukuyama Mitsunobu reaction. As will be understood by the skilled artisan, with slight modification, the intermolecular solution phase Fukuyama-Mistsunobu reaction set forth in the following references may also be used for the present cyclization: *Org. Biomol. Chem.* 2005, 3, 1049-1057; *Bioorganic & Medicinal Chemistry Letters* 2005, 18, 336-343; *Chem. Asian J.* 2007, 2, 1340-1355; *Org. Lett.* 2008, 10(1), 37-40; *Chem. Pharm. Bull.* 2005, 53(11), 1508-1509; *J. Org. chem.* 2004, 69(10), 3336-3339; and *Journal of Fluorine Chemistry* 2007 128, 595-607. Likewise, the intermolecular solid phase Fukuyama-Mistsunobu reaction disclosed in the following references may also be adapted for intramolecular cyclization: *Tetrahedron* 2005 61, 6046-6055; *Tetrahedron Letters* 2000, 41, 3309-3313; *Org. Lett.*, 2006, Vol. 8, No. 15, pp-3371; *J. Org. Chem.* 2002, 67, 8820-8826; *Chem. Commun.* 2004, 353-359; *J. Med. Chem.* 2006, 49(23), 6888-6896.

Step 3a. Intermolecular N-Alkylation Procedures

The intermolecular N-alkylation of compound (A) by compound (B) (where Z is a Br) to give compound (D) can be conducted according to the procedure disclosed in *J. Org. Chem.*, 2004, 69(10), 3530-3537 using an alkali metal carbonate. Alternatively, the N-alkylation can be achieved using an alkali metal hydroxide in a polar aprotic solvent in the presence of a drying agent, e.g., LiOH, DMF, and molecular sieves (e.g., 4 Å), as disclosed in *Org. Biomol. Chem.*, 2007, 1915-1923; or the process disclosed in *Chem. Commun.* 2004, 6, 672-673; or *Tetrahedron*, 2002, 58, 2627-2640.

Step 3b. Intermolecular N-Alkylation of N-Nosyl Peptides with Alkyl Bromides The intermolecular N-alkylation of N-Nosyl peptide compound (A) by compound (B) (where Z is a Br) to give compound (D) can be conducted according to the procedure disclosed in e.g. *Chem.-Eur. J.* 2007, 13(5), 1358-1373; and *Tetrahedron* 2008, 64(36), 8411-8416 using an alkali metal carbonate such as $K_2CO_3$ or $Na_2CO_3$ mixed at r.t. or at lower temperatures in a suitable solvent such as DMF, acetone, ethylmethyl ketone, acetonitrile, etc. in the presence or absence of additives such as KI, NaI, etc. and stirred at r.t. or higher temperatures up to 80° C.

Step 3c. Intermolecular N-Alkylation of N-Nosyl Peptides with Alcohols

The intermolecular N-alkylation of N-nosyl alcohols can conducted using the Fukuyama Mitsunobu reaction, either in solution phase or on solid phase using reagents such as $PPh_3$ (3 eq.), DEAD (or DIAD) (2 eq.), DIPEA (or TEA) (3 eq.) in a solvent such as THF. General procedures for carrying out this step in solution are disclosed in the following references: *Org. Biomol. Chem.* 2005, 3, 1049-1057; *Chem. Asian J.* 2007, 2, 1340-1355; *Chem. Pharm. Bull.* 2005, 53(11), 1508-1509; and *Journal of Fluorine Chemistry* 2007 128, 595-607. The intermolecular solid phase Fukuyama-Mistsunobu conditions disclosed in the following references may also be used: *Tetrahedron* 2005 61, 6046-6055; *Tetrahedron Letters* 2000, 41, 3309-3313; *Org. Lett.*, 2006, Vol. 8, No. 15, pp-3371; *J. Org. Chem.* 2002, 67, 8820-8826; *Chem. Commun.* 2004, 353-359; *J. Med. Chem.* 2006, 49(23), 6888-6896.

Step 4. Reductive Amination

Where Z is a carbonyl, compound (D) may be produced by reductive amination of compound (A) with compound (B) according to well known procedures (e.g., *J. Am. Chem. Soc.* 2007, 129(45), 13792-13793; *Organometallics* 2006, 25(17), 4079-4089; *J. Org. Chem.* 2002, 67(14), 5022-5024; *J. Org. Chem.* 1997, 62(6), 1841-1842; *Macromolecules*, 2007, 40(5):1480-1488; and *Org. Lett.*, 2003, 5(22):4227-4230 wherein, the compounds (A) and (B) are mixed with reducing agents such as, and not limited to, $NaBH_4$, $NaBH_3CN$, $NaB(OAc)_3H$, $Zn(BH_4)_2$ or $LiAlH_4$, at room temperature. or at lower temperatures in the presence or absence of an acid such as TsOH, AcOH, and the like in a solvent such as DCM, MeOH, DMF, etc. in the presence or absence of drying agents such as $Na_2SO_4$, $MgSO_4$ or molecular sieves (e.g. 4A) and stirred at r.t. or at higher temperatures up to 60° C.

Step 5. Macro Lactamization

Compounds of formula (D) can be cyclized to the constrained peptide of Formula I using the macro lactamization process disclosed in, e.g., *J. Am. Chem. Soc.*, 2007, 129(14), 4175-4177. Thus, $PG_3$ may first be removed using the appropriate conditions (e.g., acid for Boc groups). Subsequently, a dilute solution of the amino peptidic acid or its salt in a suitable solvent such as, e.g. DMF is cooled to about 0° C. A peptide coupling additive such as HOBT is added followed by a peptide coupling agent such as EDC, followed by a base (e.g., DIEA or another suitable secondary amine). Alternatively, the compound of formula A can also be cyclized to the constrained peptide of formula I using the procedure described in *J. Am. Chem. Soc.* 2005, 127(18), 6563-6572 using BOP as the coupling agent.

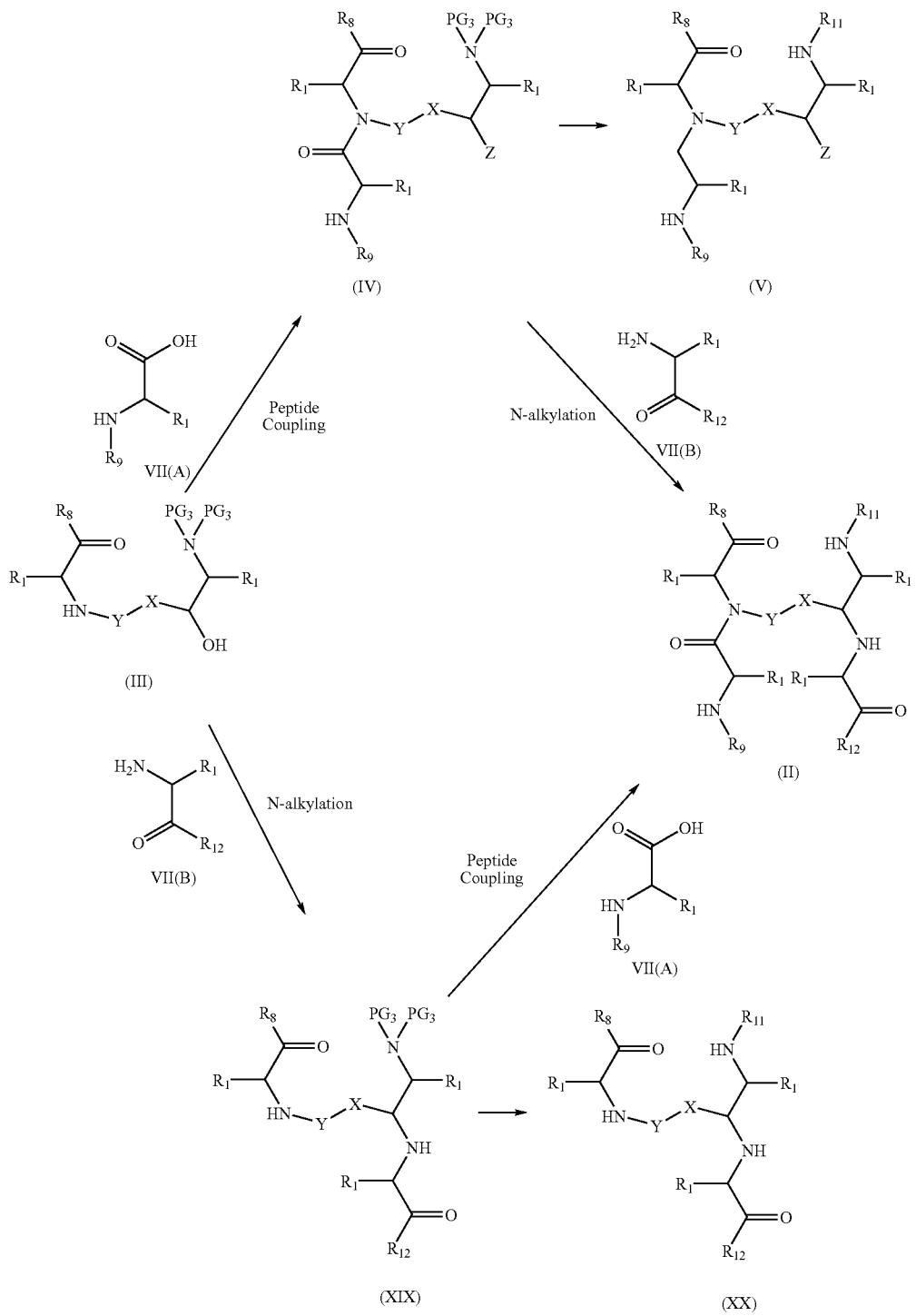

Scheme 2

As shown in Scheme 2, individual peptides linked by a covalent hydrogen-bond mimic can be synthesized starting from a simple, constrained peptide mimetic of structure III. Both peptidic or non-peptidic extensions can be added at either or both termini of the constrained peptide of Formula III. Thus, compounds of Formula II, IV, V, XIX or XX can be made by the standard peptide synthesis methods starting from a compound of Formula III. For example, the compound of Formula III, directly, or after converting the hydroxyl group to a leaving group or protecting it, can be subjected to peptide coupling with compound VII(A) to give compound IV, which can be further subjected to N-alkylation with compound VII(B) in presence of a base, followed by removal of the amino-protecting groups to give a compound of Formula II. In the scheme above, $PG_3$ at each occurrence is independently an amino protecting group; or two $PG_3$ groups may represent a single divalent amino protecting group or may represent H and an amino protecting group. The compound of Formula IV can also be directly subjected to deprotection of amino protecting group(s) to give the compound of Formula V.

Alternatively, the compound of Formula III, as such, or after converting the hydroxyl group to a leaving group or protecting it, can be first subjected to N-alkylation with compound VII(B) in presence of a base to give compound XIX, which can be further subjected to peptide coupling with compound VII(A) and deprotection of amino group to give a compound of Formula II. The compound of Formula XIX can also be directly subjected to deprotection to give a compound of Formula XX. The various steps of peptide chain extension at any of the $R_8$, $R_9$, $R_{11}$, $R_{12}$ variables can be conducted using standard methods for peptide coupling (SPPS using Fmoc or Boc) or N-alkylation (with alkyl bromide in presence of a base or with N-nosyl protected peptides) or by reductive amination of corresponding carbonyl derivatives to produce various compounds of Formula II.

Accordingly, by selectively coupling the beta-hydroxy compound of formula III with either the N-terminus of a peptide or a C-terminus of a peptide, constrained peptides having unique sheet structures can be obtained. Further, substituted halo-derivatives of compounds of Formula III, IV, V, XIX and X can also be cyclized with the N-terminus of one of the peptides to give a turn-containing peptide, such as compound of Formula I. Thus, merely by changing the sequence and type of reactions, various kinds of conformationally constrained peptide mimetic compounds can be synthesized, while retaining all the native amino acids in the sequence. This feature allows stabilization of relatively short peptide sequences from proteins in their native-like secondary structures (as judged by NMR or X-ray structures). The presently claimed methods allow the secondary structure to be established into the shortest possible sequence of amino acids from the protein which is being mimicked.

The starting polyfunctional, protected amino alcohols of Formula III can be prepared by the following method.

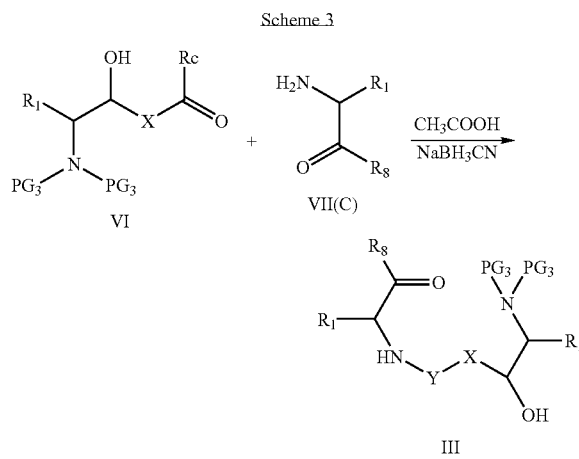

As shown in Scheme 3, compounds of Formula III can be prepared by contacting a compound of Formula VI with a compound of Formula VII(C) under reductive amination conditions (e.g., in presence of, e.g., acetic acid and sodium cyanoborohydride) to give the polyfunctional, N-protected amino alcohol of Formula III. The variables of Formulas III, VI, and VII(C) are as defined herein. Other reducing agents and conditions known in the art may also be used for this transformation. Optionally, the compounds of Formula VI may be converted to the corresponding beta-halo carbonyl compounds as disclosed herein to provide the corresponding halogenated derivatives of Formula III.

The starting polyfunctional, N-protected beta-hydroxy carbonyl compounds of Formula VI can be prepared by various methods as illustrated in Schemes 4 and 6 below.

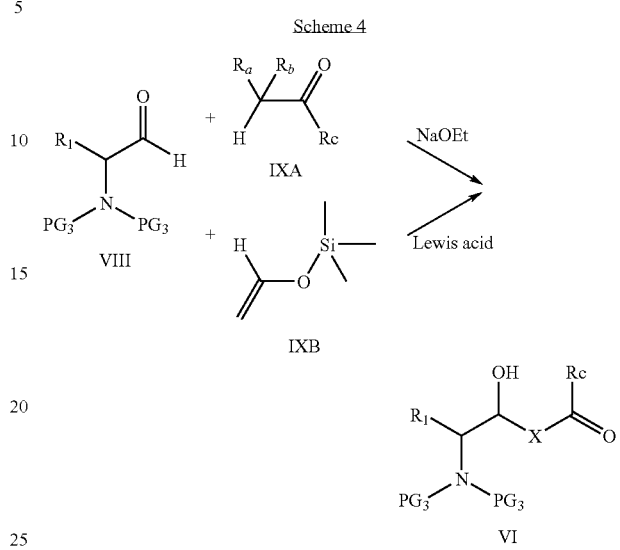

As shown in Scheme 4, N-protected, beta-hydroxyl carbonyl compounds of Formula VI can be prepared by various methods starting from N-protected carbonyl compound of Formula VIII. Thus, a compound of Formula VIII may be coupled with a compound of Formula IX(A) or IX(B) to give the compound of Formula VI. For example, compound VIII can be subjected to cross aldol reaction with a ketone or aldehyde of Formula IXA in presence of an alkali metal alkoxide to give compound VI. Alternatively, compound VIII can be subjected to Mukaiyama Aldol Reaction with a silyl enol ether of Formula IXB in presence of a Lewis acid such as boron trifluoride or titanium chloride to give N-protected, beta-hydroxy carbonyl compounds of Formula VI. Preparation of compound VIII is described in Scheme 5.

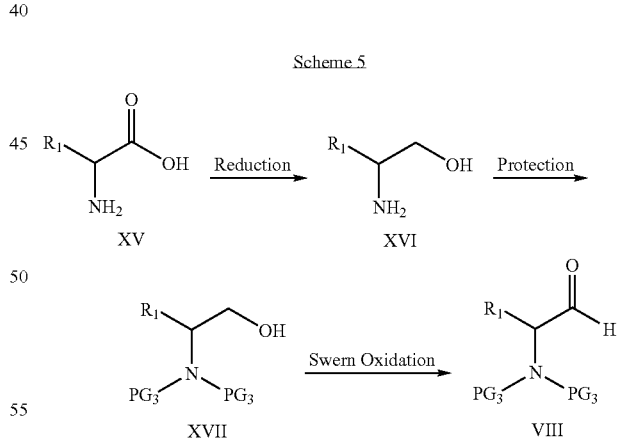

As shown in Scheme 5, N-protected carbonyl compounds of Formula VIII can be prepared starting from simple amino acids of Formula XV. These amino acids can be first reduced to the corresponding amino alcohols of Formula XVI by, e.g., using reducing agents such as $NaBH_4$—$I_2$ in THF (McKennon, M. J. et al., *J. Org. Chem.*, 1993, 58, 3568-3571). The amino group of these amino alcohols can then be protected by standard methods known in the art. The N-protected amino alcohol of Formula XVII is then oxidized, e.g., by use of the Swern oxidation using oxalyl chloride, dimethyl sulfoxide (DMSO) and an organic base, such as triethylamine.

Scheme 6

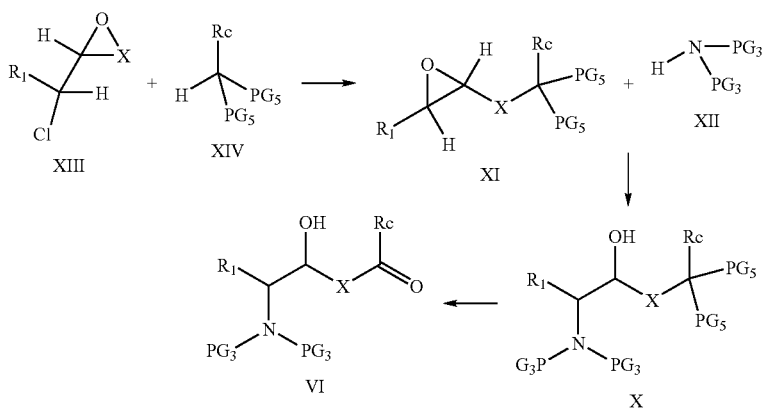

As shown in Scheme 6, N-protected beta-hydroxy carbonyl compounds of Formula VI can also be prepared from substituted epichlorohydrins. Substituted epichlorohydrins of Formula XIII upon contacting with a suitable nucleophilic reagent of Formula XIV give a protected epichlorohydrin of Formula XI, which on further nucleophilic ring opening with a protected amino compound of Formula XII gives a N- and carbonyl protected secondary alcohol of Formula X. Compound X on removal of the carbonyl group protection gives N-protected beta-hydroxy carbonyl compounds of Formula VI.

Scheme 7

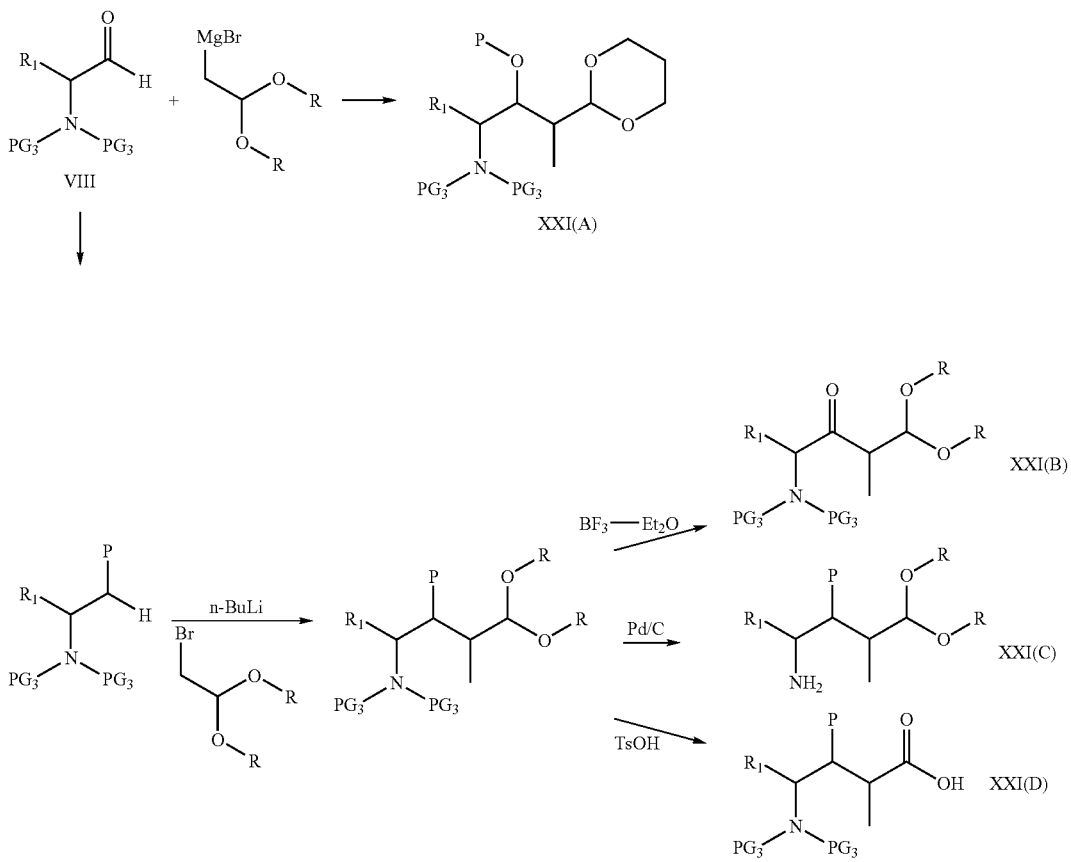

As shown in Scheme 7, various synthons or precursors similar to compound VI, such as, compounds XX(A), XX(B), XX(C), and XX(D) can also be prepared starting from simple N-protected carbonyl compound of Formula VIII using various reactions such as Grignard's reaction, $BF_3$-$Et_2O$ catalyzed C—C bond formation, reductive removal of N-protecting groups with Pd/C and deprotection of O with TsOH.

Synthetic nonpeptide molecules can then be produced based upon information obtained from nuclear magnetic resonance (NMR) to determine binding interactions and bound-state conformations of these structures; and employing molecular modeling to interpret the NMR data and to predict improved synthetic nonpeptide structures.

NMR conformational analysis for small peptide and peptide analog systems in solution is straightforward and well known in the art. For example, see Bax, Two-Dimensional Nuclear Magnetic Resonance in Liquids, D. Reidel Publishing Co., Boston, 1982; Wuthrich, NMR of Proteins and Nucleic Acids, Wiley-Interscience, New York, 1986; Ernst et al., Principles of Nuclear Magnetic Resonance in One and Two Dimensions, Oxford University Press, New York, 1987.

NMR along with computer-assisted molecular modeling allows the identification of ligand-receptor interactions required for binding. Identifying the interactions required for binding facilitates preparation of synthetic molecules that are capable of similar binding, and therefore of acting as agonists or antagonists. Once a single stable binding conformation is known, the design and preparation of a synthetic therapeutic molecule capable of acting as an agonists or antagonist is thus brought within the ability of one skilled in the art, without requiring undue experimentation.

Thus, in another aspect, the technology provides synthetic therapeutic molecules capable of acting as agonists or antagonists, wherein such molecules are based upon structural features of a conformationally restricted beta-turn mimetic that is capable of binding to the receptor. Particularly likely candidates for the development of such therapeutics include synthetic molecules based upon one or more structural features of a binding conformation of a peptide hormone, lymphokine, growth factor, enzyme inhibitor, or viral binding protein.

The constrained peptide mimetics of this technology have broad utility in a variety of naturally occurring or synthetic peptides and proteins. In one aspect, the current technology replaces the i>i+n hydrogen bonding interaction along the backbone of peptides with a covalent mimic.

For example, the technology provides both beta-turn mimetics having variable sizes and bond angles and variable side chain constituents, and peptides containing such beta-turn mimetics internally or at either end or at the end, connecting both the termini. An advantage of the present technology is that such constrained beta-turn mimetics are made directly from native peptide sequences that are contained in natural agonists and antagonists, i.e., there is no need to first search for a drug lead. The natural sequence of the native peptide being mimicked in the biological system is itself the drug lead, and is constrained by this technology without mutation of any of its structural features. Hence, the molecular recognition surface of the natural substrate is completely retained. Such beta-turn mimetics, or peptides containing the same, are conformationally restricted, and as such are useful for the design and synthesis of conformationally restricted antigens for making synthetic vaccines or for making antibodies for diagnostic purposes.

Additionally, such beta-turn mimetics are useful for mapping critical receptor-ligand interactions for purposes of designing nonpeptide therapeutics. They are useful not only for initial mapping, based upon which beta-turn mimetics bind the receptor, from knowledge of the natural peptide sequences that bind to the receptors or the biological target, but are also useful for subsequent investigation directed toward identification of molecular interactions and conformations critical to the binding. For example, if a beta-turn mimetic represented by the structural formula Ala-Phe-Trp-Lys-Thr-Ala (SEQ ID NO: 8) (containing the Phe-Trp-Lys-Thr (SEQ ID NO: 1) tetrapeptide pharmacophore of Somatostatins) was found to bind to a receptor of interest, the significance of particular hydrogen bonds in its binding, for example between the side chain of Thr and either the carbonyl of the peptide of Trp or the carbonyl of the peptide of Phe, can easily be tested by preparing an analog of the beta-turn mimetic that cannot form these bonds, for example Ala-Phe-Trp-Lys-Ala-Ala (SEQ ID NO: 9).

In another example, if multiple conformations and the associated topologies are possible for a constrained peptide, those conformations or topologies or related structures essential for a specific biological activity can be determined by synthesizing different topological isomers of the constrained peptide. For example, five different topological dispositions of the same beta-turn-forming pharmacophore tetra peptide FWKT (SEQ ID NO: 1) in somatostatin hormones are responsible for activating the different human somatostatin receptors 1-5 and inducing various responses in the G-protein signal cascade that result in several physiological functions including the regulation of growth hormone stimulation and insulin expression. Specific topological mimics of the constrained β-turn analogues of somatostatin are excellent for selectively inducing the different above mentioned responses in cells (for illustrative examples see J. Med. Chem., 1998, 42:919-929; J. Med. Chem., 1998, 42:1146-1154; J. Med. Chem., 1998, 42:2175-2179; J. Med. Chem., 1998, 42:2679-2685; J. Med. Chem., 1998, 42:2686-2692; J. Med. Chem., 1998, 42:4693-4705; J. Med. Chem., 1998, 51(5):1223-1230; and J. Med. Chem., 2005, 48(21):6643-6652). Similarly, topological mimics of the specific topological isoforms of the MSH tetrapeptide pharmacophore are good leads for various responses in cells. For examples of MSH analogues, see Peptides, 2005, 26(10):1687-1689.

In another aspect of the technology, constrained peptides that are structural analogues of sheet forming peptides with antimicrobial activity can be synthesized. For example, the β-sheet forming cyclic decapeptide homodimer Gramicidin-S has two turns and an antiparallel β-sheet in it and is an excellent antimicrobial peptide. But the natural peptide is digested in a very short time in the human system and hence nonpeptide analogues of Gramacidin-S are sought after. The technology can be used to synthesize several nonpeptide reverse turn/sheet analogues of Gramacidin-S as antimicrobial drug leads.

Table 1 lists illustrative peptides that can be modified with one or more hydrogen bond mimics disclosed herein to provide compounds of the technology. Table 1 also includes the biological targets that such compounds may act upon.

| Seq ID. No. | Peptide | Target Domain/Cell | Therapeutic target | Reference |
|---|---|---|---|---|
| | β-turn/β-hairpin/β-sheet | | | |
| | Somatostatin | | | |
| 1 | FWKT | Human somatostatin receptor | G-protein signal cascade | (Examples of analogues containing FWKT (SEQ ID NO: 1)) J. Med. Chem., 1998, 42: 919-929; 1146-1154; 2175-2179; 2679-2685; 2686-2692; 4693-4705; J. Med. Chem., 2005, 48(21): 6643-6652; J. Med. Chem., 2008, 51(5): 1223-1230 |
| 2 | F$^D$WKT | Human somatostatin receptor | G-protein signal cascade | 17 |
| | Gramidicin-S | Cell membrane | Antimicrobial | 18 |
| 3 | Analogues of $_{Cyclo}$[$^D$FPVOL]$_2$ | Cell membrane | Antimicrobial | For a few analogues of GS see: Biophysical Journal, 2008, 95(7): 3306-3321; Peptide Science, 2007, 44: 255-256; Journal of Antibiotics, 2006, 59(6): 370-372 |
| 4 | NPNA - Circumsporozite surface protein of the malarial parasite - P. falciparum - β-turn | | T-cell epitope in multiple antigen peptide | J. Am. Chem. Soc., 1998, 120: 7439-7449 |
| 5 | HFRW - pharmacophores in MSH and ACTH (G-protein coupled receptors) | MCHs - hormones for melanocortin receptors 1-5 | Pigmentation, anti obesity, cardiovascular regulation | Peptides, 2005, 26(10): 1687-1689 |
| | Met represser - β-sheet peptides (in E. coli) | dsDNA | DNA recognition and Gene regulation | Nature, 1992, 359(6394): 431-433; Nature, 1992, 359(6394): 387-393; J. Nol. Biol., 1992, 226(4): 1257-1270 |
| | γ-turn | | | |
| 6 | MpaYFQNCP$^D$RG-NH$_2$ (Desmopressin) - Int. J. Pept. Protein Res. 1985, 25, 561-574 - a drug analogue of Vasopressin | | Antidiuretic, treatment of mild haemophilia A, von Willebrand's disease and thrombocyte dysfunction | For example of an analogue - Chem. Eur.J., 1999, 5(8): 2241-2253 |
| 10 | CYFQNCPRG-NH$_2$ (a neurohypophyseal peptide hormone) - J. Am. Chem. Soc. 1953, 75, 4880 ± 4881 Please note the modified sequence. | | | |
| 7 | GPG(R/Q)PGQ - β-hairpin; V3 loop of gp120 (HIV-1) PND (principle Neutralizing domain) | | HIV-1 | Biochemistry, 2006, 45(13): 4284-4294 |
| 11 | Y$^D$WKT | Human somatostatin receptor | G-protein signal cascade | PNAS USA 1998, 95, 10836-10841; |
| 12 | Y$^D$WKV | Human somatostatin receptor - Antitumor | G-protein signal cascade | PNAS USA 1998, 95, 1794-1799; |

In a further aspect of this technology, methods for screening compounds disclosed herein for bioactivity and isolating bioactive compounds are disclosed. Compounds of the present technology may be screened for bioactivity by a variety of techniques and methods. Generally, the screening assay may be performed by (1) contacting a compound or a library (i.e. collection or group) of such compounds with a biological target of interest, such as a receptor, and allowing binding to occur between the compound or members of the library and the target, and (2) detecting the binding event by an appropriate assay, such as by the colorimetric assay disclosed by Lam et al. (Nature 354:82-84, 1991) or Griminski et al. (Biotechnology 12:1008-1011, 1994) (both of which are incorporated herein by reference). In one embodiment, the library members are in solution and the target is immobilized on a solid phase. Alternatively, the library may be immobilized on a solid phase and may be probed by contacting it with the target in solution. Biological targets of interest include those set forth in Table 1 above.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present compounds, thus generally described, will be understood more readily by reference to the following examples, which are provided by way of illustration and are not intended to be limiting of the present invention.

EXAMPLES

The present technology is further illustrated by the following examples, which should not be construed as limiting in any way.

The following abbreviations are used throughout the present disclosure with respect to bio-chemical terminology:
ACN: Acetonitrile
AcOH: Acetic acid
Aib: α-aminoisobutyric acid
Ala Alanine
Boc: N-tert-Butoxycarbonyl Bop Benzotriazole-1-yl-oxy-tris-(dimethylamino)-phosphonium hexafluorophosphate
Bn: Benzyl
Bu: Butyl
Cbz or Z: Benzoyloxycarbonyl
DCC: Dicyclohexylcarbodiimide
DCM Dichloromethane
DEAD Diethyl azodicarboxylate
DIAD Diisopropyl azodicarboxylate
DIEA Diisopropylethylamine
DIPEA Diisopropyl ethylamine
DMAP: N,N-dimethyl-4-aminopyridine
DMF: N,N-Dimethylformamide
ECF Ethyl chloroformate
Et: Ethyl
EtOAc: Ethyl acetate
EtOH: Ethanol
Fmoc: Fluorenyl-methoxy-carbonyl
HATU: O-(7-Azabenzotriazole-1-yl)-N,N,N'N'-tetramethyluronium hexafluorophosphate
HBTU: O-(1H-Benzotriazole-1-yl)-N,N,N',N'-tetramethyluronium hexafluorophosphate
HOBt: 1-Hydroxybenzotriazole
HOSu Hydroxy-succinimide
HPLC: High Pressure Liquid Chromatography
IPA: Iso-propyl alcohol
$K_2CO_3$ Potassium carbonate
LiOH Lithium hydroxide
Me: Methyl
MS (ESI): Electrospray ionization mass spectrometry
$Na_2CO_3$ Sodium carbonate
$NaHCO_3$ Sodium bicarbonate
Nosyl (Ns) 4-nitrobenzenesulfonyl
NMM: N-Methylmorpholine
NMR: Nuclear Magnetic Resonance
Ph: Phenyl
$PPh_3$ Triphenyl phosphine
PhSH Thiophenol
r.t. Room temperature
SLC: Side-chain linked
SPPS: Solid phase peptide synthesis
tBu: tert-butyl
TFA: Trifluoroacetic acid
THF: Tetrahydrofuran
TLC Thin layer chromatography Example 1

Amide Bond Coupling Reaction Between Carboxylic Acid and Alkyl Amine

Example 1A

General Protocol for Peptide Coupling Reaction

A solution of N-protected amino acid or peptidic carboxylic acid (1 eq.) in THF (0.1-0.3 M) is cooled to −15° C. and stirred under nitrogen atmosphere. NMM (1.2 eq.) is added to the solution, followed by ethyl chloroformate (1.03 eq.) and is stirred. After exactly 2 minutes, a 0.1 M solution of the amine hydrochloride (1.1 eq.) in THF:DMF (4:1) is added along with NMM (2.2 eq.) and stirred for 15 minutes. The mixture is allowed to warm to room temperature and is stirred until TLC indicates the complete consumption of the starting acid (~3-5 h). The solvents are removed under vacuum and the residue is diluted with EtOAc and is washed with brine, water, citric acid and saturated $NaHCO_3$ solutions. The organic layer is concentrated under vacuum to yield a residue. Purification by silica gel flash column chromatography using hexanes:EtOAc gives the desired peptide in high yields.

Example 1B

Synthesis of Boc-Ala-Ala-Ala-NH—$(CH_2)_4$—Br

Step I: Synthesis of Boc-Ala-OH

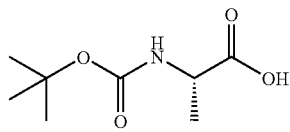

$K_2CO_3$ (3.1 g, 22.46 mmol) and alanine (1 g, 11.23 mmol) were dissolved in minimum amount of water (8 mL) maintained at 0° C. A solution of ditertiarybutyl dicarbonate (2.57 g, 11.8 mmol) in THF (4 mL) was slowly added to the aqueous solution and stirred. Additional amounts of $K_2CO_3$ were added, if needed, to the mixture in order to maintain the pH of the solution between 10-12. After stirring at 0° C. for 30 minutes, the mixture was warmed to r.t. After eight hours THF was removed under reduced pressure and the aqueous portion was washed with diethyl ether, acidified (to pH 2) with citric acid and extracted with ethyl acetate (3×10 mL). The organic layer was dried over $Na_2SO_4$ and concentrated under vacuum to give a white solid (m.p. 77-79° C.) in quantitative yields (2.12 g).

HRMS (EI) m/z calculated for $C_8H_{15}NNaO_4$—212.0899, Found—212.0899.

Step II: Synthesis of ClH.AlaOMe

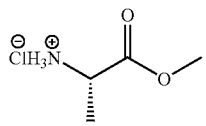

To a suspension of alanine (650 mg, 7.29 mmol) in methanol (8 mL) at 0° C. was added $SOCl_2$ (0.54 mL, 8.02 mmol) drop wise at a rate so that the temperature of the reaction mixture does not exceed 4° C. 5 min after complete addition, the ice bath was removed and the reaction mixture was stirred at 25° C. for 8 hrs, followed by removal of the solvent under vacuum through a $KOH/CaCl_2$ tower to give the desired methyl alaninate hydrochloride as white hygroscopic solid in quantitative yield (1.01 g).

IR (NaCl, neat) ν: 3414.6, 2959.2, 1747.3, 1616.3, 1515.7, 1459, 1252, 1215.9, 1118 cm$^{-1}$; LRMS (EI) m/z calculated for C$_4$H$_9$NO$_2$—103.0633, Found—104 [M+H]$^+$ (100%); 207 [2M+H]$^+$ (100%).

Step III: Synthesis of Boc-Ala-Ala-OMe

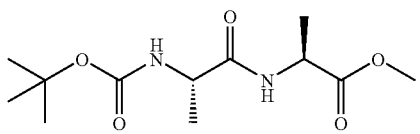 [SMILES: COC(=O)[C@H](C)NC(=O)[C@H](C)NC(=O)OC(C)(C)C]

To a cold (−15° C.) solution of Boc-Ala-OH (1.034 g, 5.47 mmol) and NMM (901 μl, 8.20 mmol) in THF (15 mL) was added ECF (538 μl, 5.63 mmol) under N$_2$ atmosphere and vigorously stirred. After 2 min of stirring, a solution of methyl alaninate hydrochloride (840 mg, 6.01 mmol) in a mixture of solvents THF:DMF (4 mL:3 mL) was added to the reaction mixture followed by NMM (1.5 mL, 13.67 mmol) and stirred. After 10 min the mixture was warmed to 25° C. and stirred for further 8 h. THF was removed under reduced pressure and the resulting viscous solution was diluted with water (10 mL) and thoroughly extracted with ethyl acetate. The combined organic extracts were washed with saturated citric acid (10 mL), saturated NaHCO$_3$ (10 mL) and dried over by Na$_2$SO$_4$ and concentrated under reduced pressure to give a residue, which was purified by silica gel flash column chromatograph (EtOAc:Hexane—3:17) to give the desired product as a solid (m.p. 107-108° C.) in good yields (1.48 g, 98.6%). (TLC: EtOAc:Hexanes 7:3—R$_f$—0.55).

IR (NaCl, neat) ν: 3315, 2982, 2938, 1746, 1693, 1668, 1533, 1249, 1213, 1167, 1070, 1054 cm$^{-1}$. $^1$H NMR (400 MHz, CDCl$_3$) δ ppm: 6.69 (bs, 1H), 5.05 (bs, 1H), 4.56 (quint, J=7.2 Hz, 1H), 4.20-4.10 (m, 1H), 3.74 (s, 3H), 1.44 (s, 9H), 1.39 (d, J=7.2 Hz, 3H), 1.35 (d, J=7.1 Hz, 3H). $^{13}$C NMR (100 MHz, CDCl$_3$) δ ppm: 173.2 (2C), 172.2, 80.1, 52.5, 49.9, 48.0, 28.3, 18.3, 18.2. HRMS (EI) m/z calculated for C12H22N2NaO5: 297.1426, Found: 297.1432 [M+Na]$^+$.

Step IV: Synthesis of Boc-Ala-Ala-OH

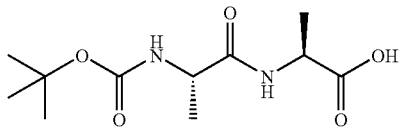 [SMILES: C[C@H](NC(=O)[C@H](C)NC(=O)OC(C)(C)C)C(=O)O]

To a solution of LiOH.H$_2$O (275 mg, 6.56 mmol) in a mixture of solvents MeOH:H$_2$O (10.9 mL:3.6 mL) was added Boc-Ala-Ala-OMe (1.2 g, 4.38 mmol) and stirred for 4 hours at r.t. The solution was acidified to pH 2 with saturated aqueous solution of citric acid and the mixture was extracted with EtOAc (3×20 mL). The organic layer was dried over Na$_2$SO$_4$ and concentrated under vacuum to give the desired product Boc-Ala-Ala-OH as a highly viscous and hygroscopic oil in quantitative yields (1.14 g). The product was taken for further reactions directly without any purification.

Step V: Synthesis of Boc-Ala-Ala-NH—(CH$_2$)$_4$—OH

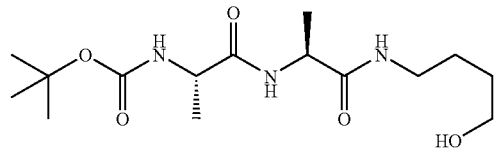 [SMILES: C[C@H](NC(=O)OC(C)(C)C)C(=O)N[C@@H](C)C(=O)NCCCCO]

To a vigorously stirring solution of Boc-(Ala)$_2$-OH (0.9 gm, 3.46 mmol) and NMM (0.57 mL, 5.2 mmol) in THF (20 mL) cooled to −15° C. was added under N$_2$ atmosphere ethyl chloroformate (ECF) (372 μL, 3.56 mmol) and stirred for 2 min. A solution of H$_2$N(CH$_2$)$_4$OH (462 mg, 5.19 mmol) in THF (5 mL) was added to the mixture followed by NMM (950 μL, 8.65 mmol) and the mixture was warmed to r.t. and stirred until silica gel TLC indicated complete consumption of the starting acid (eluting solvent—MeOH:DCM—1:10, R$_f$—0.45) (~8 h). The solvent was evaporated, and the residue was diluted with EtOAc and washed with brine, water, saturated solutions of citric acid and NaHCO$_3$, and the organic layer was dried using NaHSO$_4$, and the solvent was removed under vacuum to yield a residue which was purified using silica gel flash column chromatography—Hexanes:EtOAc—1:3; to give the desired product in 75% yield (858 mg) as a solid—m.p.—102-104° C.

IR (NaCl, neat) ν: 3300.3, 2978.6, 2939.9, 2875.7, 1654.5, 1531.6, 1452.9, 1368.2, 1250.4, 1167.7, 1021.2 cm$^{-1}$. $^1$H NMR (300 MHz, CDCl$_3$) δ ppm: 7.11 (bs, 1H), 7.04 (bs, 1H), 5.33 (bs, 1H), 4.46 (quint., J=7.2 Hz, 1H), 4.21-4.13 (m, 1H), 3.64 (t, J=5.7 Hz, 2H), 3.27 (q, J=6.0 Hz, 2H), 3.20-2.80 (bs, 1H), 1.63-1.57 (m, 2H), 1.44 (s, 9H), 1.37 (dd, J=6.6 Hz, 3.3 Hz, 6H). $^{13}$C NMR (75 MHz, CDCl$_3$) δ ppm: 172.7, 172.1, 155.5, 80.5, 62.1, 50.6, 49.0, 39.2, 29.7, 28.3, 25.9, 18.3, 18.2.

Step VI: Synthesis of Boc-Ala-Ala-NH—(CH$_2$)$_4$—Br

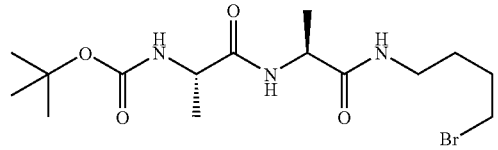

To a solution of Boc-Ala-Ala-NH—(CH$_2$)$_4$—OH (500 mg, 1.51 mmol) and PPh$_3$ (792 mg, 3.02 mmol) in THF (10 mL) at −15° C. was added a solution of NBS (321 mg, 2.72 mmol) in THF (5 mL) and stirred until TLC (MeOH:DCM—1:10—R$_f$—0.60) indicated complete consumption of the starting amino alcohol (45 min). The solvent was evaporated under vacuum and the residue was diluted with ethyl acetate and washed with water. The organic layer was dried over Na$_2$SO$_4$ and concentrated to give a residue that was purified by silica gel flash column chromatography—EtOAc:Hexanes—3:7, to yield the desired bromide as a solid (m.p. 141-142° C.) in 73% yield (416 mg).

IR (KBr) ν: 3290.9, 2979, 2923, 1641.1, 1541, 1044.3 cm$^{-1}$. $^1$H NMR (300 MHz, CDCl$_3$) δ ppm: 6.76 (b, 2H), 5.06

(d, J=6 Hz, 1H), 4.39 (quin, J=6.6 Hz, 1H), 4.10 (quin, J=6.9 Hz, 1H), 3.39 (t, J=6.6 Hz, 2H), 3.12 (m, 2H), 1.85 (m, 2H), 1.64 (m, 2H), 1.42 (s, 9H), 1.36 (d, J=7.2 Hz, 3H), 1.34 (d, J=6.9 Hz, 3H). HRMS (EI) m/z calculated for $C_{15}H_{28}BrN_3O_4$—393.1263, Found: 416.1157 [M+Na]$^+$, 418.1111 [M+2H+Na]$^+$. $^{13}$C NMR (75 MHz, CDCl$_3$:CD$_3$OD 24:1) δ ppm: 173, 172, 156, 81, 51, 50, 39, 33, 29, 28.4, 28.3, 28, 18.

Step VII: Synthesis of TFA-H-Ala-Ala-NH—(CH$_2$)$_4$—Br

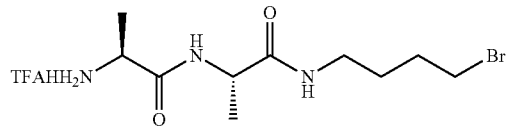

The desired compound (TFA-H-(Ala)$_2$-NH—(CH$_2$)$_4$—Br) was synthesized by the general procedure for Boc-deprotection (described earlier) of the corresponding Boc-protected peptide precursor. A typical experiment at 210 μmol scale was complete in 3.5 h and yielded the desired product (100%) without any purification after removal of solvent under high vacuum. The resulting residue was taken up directly for coupling in the next step. TLC (MeOH:DCM—1:9; R$_f$=0.35).

Step VIII: Synthesis of Boc-Ala-Ala-Ala-NH—(CH$_2$)$_4$—Br

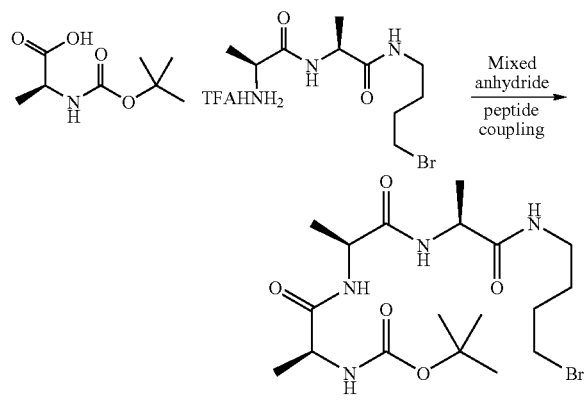

To a cold (−15° C.) solution of Boc-Ala-OH (118 mg, 0.63 mmol) and NMM (103 μl, 1.03 mmol) in THF (8 mL) was added ECF (61 μl, 0.64 mmol) and stirred vigorously. After 2 min. a solution of the TFA salt of Ala-Ala-NH(CH$_2$)$_4$—Br (280 mg, 0.69 mmol) in a mixture of THF:DMF (4 mL:2 mL) was added to it followed by NMM (170 μL, 1.7 mmol) and stirred for further 30 minutes. The mixture was warmed to r.t. and stirred for 6 h. The solvent was removed under reduced pressure to give a residue which was diluted with EtOAc and washed with saturated citric acid, saturated NaHCO$_3$ and the organic layer was dried over Na$_2$SO$_4$ and concentrated under vacuum to give a residue, which was purified by silica gel flash column chromatography (EtOAc:Hexanes—9:1) to give the desired product as a solid (m.p.—196-198° C.) in moderate yields (137 mg, 54%). TLC (MeOH:DCM—1:9; R$_f$—0.53).

IR (NaCl, neat) ν: 3276.1, 3073.9, 2980.2, 2931.5, 1669.5, 1634.9, 1545.6, 1444.6, 1365.5, 1169.3, 1052.9 cm$^{-1}$. $^1$H NMR (300 MHz, CDCl$_3$) δ ppm: 7.25 (s, 1H), 6.82 (s, 1H), 6.58 (s, 1H), 5.03 (s, 1H), 4.33-4.539 (quin, J=7.5 Hz, 1H), 4.24-4.36 (t, J=6.9 Hz, 1H), 4.02-4.04 (m, 1H), 3.24-3.56 (m, 4H), 1.65-1.91 (m, 4H), 1.43 (s, 9H), 1.41 (m, 9H). HRMS (EI) m/z calculated for $C_{18}H_{33}BrN_4O_5$—464.1634, Found—487.1535 [M+Na]$^+$, 489.1527 [M+2H+Na]$^+$, 387.1118 [M−Boc]$^+$. $^{13}$C NMR (75 MHz, CDCl$_3$:CD$_3$OD—24:1) δ ppm: 174.2, 172.6, 156.4, 80.9, 51.3, 49.1, 44.6, 38.4, 33.3, 29.8, 28.1, 27.7, 17.4, 17.3.

Example 2

Cyclo N-Alkylation of N-Nosyl Peptidic Alkyl Bromides

Example 2A

General Protocol for Cyclo-N-Alkylation Reaction

To a 0.02 M solution of the N-nosyl peptidic alkyl bromide (1 eq.) in DMF is added K$_2$CO$_3$ (2 eq.) and the mixture stirred at room temperature until TLC indicates complete consumption of the starting material (~8 h). The mixture is diluted with ethyl acetate, filtered through celite and the organic solvents are removed under vacuum to give a residue, which is purified by column chromatography to give the desired cyclic product. The above mixture can alternatively also be heated to >70° C. to complete the reaction in ~3.5 h and give the desired product.

Example 2B

Alternative Protocol for N-Alkylation Reaction

To a 0.04M solution of the N-nosyl peptidic alkyl bromide (1 eq.) in dry DMF (0.04 M) is added Cs$_2$CO$_3$ (~25 eq.). The suspension is heated to 50° C. and agitated until TLC indicates the complete consumption (~40-150 h) of the starting N-nosyl peptidic alkyl bromide. The solvent is removed under vacuum to give a residue that is purified by silica gel flash column chromatography to yield the desired product in good yields.

Example 2C

Synthesis of [Ala-Ala-Ala-NH—(CH$_2$)$_4$]$_{cyclo}$

Step I: Synthesis of TFA Salt of H$_2$N-Ala-Ala-Ala-NH—(CH$_2$)$_4$—Br

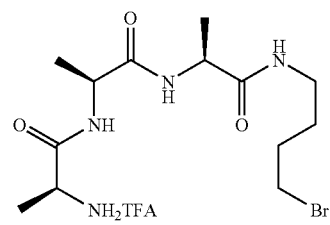

To an ice cold solution of Boc-(Ala)$_3$-NH—(CH$_2$)$_4$—Br (30 mg, 0.065 mmol) in dry DCM (3 mL) was added TFA (400 μL) and stirred for 5.5 h. The solvents were removed under vacuum to give a residue (30 mg), which was the desired product (95%) and was taken directly for synthesis in the next step. TLC—MeOH:DCM—1:4, $R_f$=0.53.

IR (NaCl, neat) ν: 3288.9, 3075.6, 2986.5, 2883.2, 2825.2, 1673.7, 1636.8, 1527.8, 1447.7, 1254.3, 1204.6, 1182.4, 1138.9 cm$^{-1}$. $^1$H NMR (300 MHz, CDCl$_3$) δ ppm: 8.24 (d, J=5.7 Hz, 1H), 7.93-7.84 (m, 1H), 4.14 (q, J=7.2 Hz, 1H), 4.02 (dq, J=7.2 Hz, 2.4 Hz, 1H), 3.89 (q, J=7.2 Hz, 1H), 3.31 (t, J=6.6 Hz, 2H), 3.10-2.98 (m, 2H), 1.67 (quint., J=6.6 Hz, 2H), 1.50-1.43 (m, 2H), 1.35 (d, J=7.2 Hz, 3H), 1.20 (dd, J=7.5 Hz, 7.5 Hz, 6H). $^{13}$C NMR (75 MHz, CDCl$_3$: CD$_3$OD—24:1) δ ppm: 175.6, 175.2, 171.4, 54.5, 50.8, 50.4, 49.7, 39.2, 35.1, 30.2, 27.9, 17.5 (2C). LRMS (EI) m/z calculated for C$_{13}$H$_{25}$BrN$_4$NaO$_3$—387, 389, Found—387, 389 [M−TFA+Na]$^+$, calculated for C$_{13}$H$_{26}$BrN$_4$O$_3$—365, 367, Found—365, 367 [M−TFA+H]$^+$, Step II: Synthesis of [Ala-Ala-Ala-NH—(CH$_2$)$_4$]$_{cyclo}$

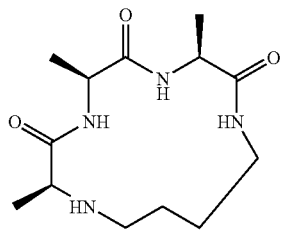 [SMILES: C[C@@H]1NCCCCNC(=O)[C@H](C)NC(=O)[C@H](C)NC1=O]

To a solution of the TFA salt of H$_2$N-Ala-Ala-Ala-NH—(CH$_2$)$_4$—Br (15 mg, 0.032 mmol) in H$_2$O (3 mL) was added NaHCO$_3$ (5 mg, 0.065 mmol) and stirred at 90° C. for 12 h. The mixture was filtered over celite, washed with MeOH and concentrated to give a residue, which was the desired product along with the corresponding product of direct hydrolysis (H-(Ala)$_3$-NH—(CH$_2$)$_4$)—OH) (9.1 mg).

HRMS (EI) m/z calculated for C$_{13}$H$_{24}$N$_4$NaO$_3$—307.1746, Found—307.1732; calculated for C$_{13}$H$_{26}$N$_4$NaO$_4$—325.1852, Found—325.1843 (100%).

Example 3

Cyclo N-Alkylation of N-Nosyl Alcohols

Example 3A

General Protocol for Cyclo-N-Alkylation Reaction

The procedure for intramolecular N-alkylation of Nosyl amides with alkyl alcohols can be achieved by following the procedure as reported in the following references: *Bioorganic & Medicinal Chemistry* 2008, 16, 4532-4537; *Tetrahedron* 2008, 64(32), 7531-7536; and *Bioorganic & Medicinal Chemistry Letters* 2008, 15, 4033-4036. Herein, to the N-nosyl amido alcohol (1 equivalent) in THF (0.1-0.3 M) is added PPh$_3$ (2-4 equivalents), DIAD or DEAD (2-4 equivalents) and the reaction is stirred until completion of the reaction (TLC indicates complete consumption of the starting bromide). Both PPh$_3$ and DIAD are added in one or several portions each in periods of 6-10 hours as is appropriately judged while following the progress of the reaction by TLC. The mixture is concentrated and purified by silica gel flash column chromatography to give the desired cyclized product.

Example 4

Intermolecular N-Alkylation of N-Nosyl Peptides with Alkyl Bromides

Example 4A

Synthesis of Boc-NH—(CH$_2$)$_4$—N(Ns)-Ala-OMe

Step I: Synthesis of Boc-NH—(CH$_2$)$_4$—Br

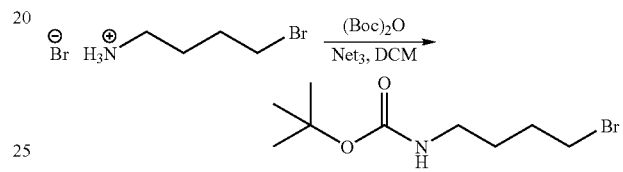

To a cold (0° C.) stirring mixture of 1-amino-4-butyl bromide hydrobromide (1 equivalent; prepared as described in *J. Org. Chem.* 2003, 68 (7), 2960-2963) and ditertiarybutyl dicarbonate (1 equivalent) in dichloromethane (~1 M) is added triethyl amine (2 equivalents) and the mixture is warmed to r.t. and stirred for further 10 h. The mixture is diluted with dichloromethane (10 mL/mmol), washed with water (2×5 mL), dried over Na$_2$SO$_4$ and concentrated under vacuum to give a residue which is purified using silica gel flash column chromatography (EtOAc:Pet. Ether) to give the desired product. (TLC-EtOAc:Pet. Ether).

Step-II: Synthesis of Boc-Ala-Ala-NH—(CH$_2$)$_4$—N(Ns)-Ala-OMe

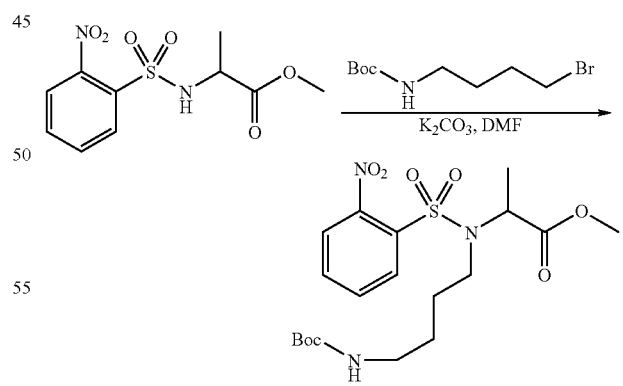

A mixture of N-Nosyl-methyl alaninate (1 equivalent) and K$_2$CO$_3$ (2 equivalents) in dry DMF (~0.3 mM) is stirred for 30 minutes followed by the addition of N-Boc-1-amidobutyl-4-bromide (1.2 equivalents). The resulting mixture is stirred vigorously for further 36 h at r.t. The mixture is diluted with water (5 mL) and extracted with ethyl acetate (3×15 mL) and the organic extracts are dried over Na$_2$SO$_4$ and concentrated under vacuum to give a residue, which is subjected to silica gel flash column chromatography (EtOAc:Pet. Ether) to give the desired product.

Example 4B

Synthesis of Boc-Ala-Ala-NH—(CH$_2$)$_4$N(Ns)-Ala-OMe

Step I: Synthesis of Boc-Ala-Ala-NH—(CH$_2$)$_4$—N(Ns)-Ala-OMe

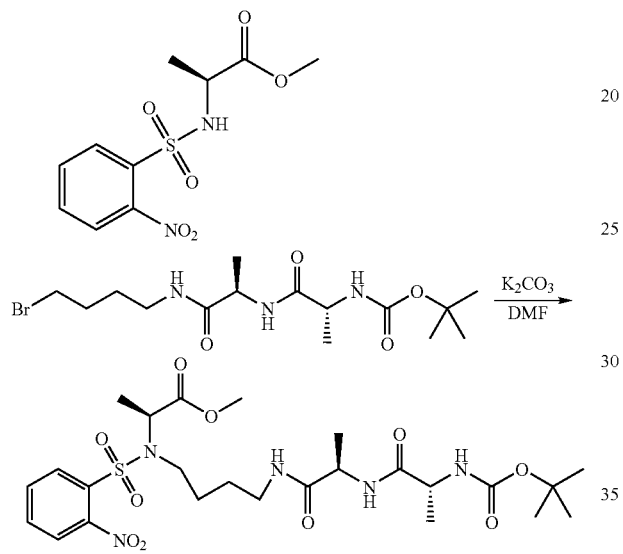

A mixture of N-Nosyl-methyl alaninate (1 equivalent) and K$_2$CO$_3$ (2 equivalents) in dry DMF (~0.3 mM) is stirred for 30 minutes followed by the addition of N-Boc-Ala-Ala-1-amidobutyl-4-bromide (1.2 equivalents; prepared as described in Step VI of Example 1B above) and is stirred vigorously for a further 36 h at r.t. The mixture is diluted with water (5 mL) and extracted with ethyl acetate (3×15 mL) and the organic extracts are dried over Na$_2$SO$_4$ and concentrated under vacuum to give a residue, which is subjected to silica gel flash column chromatography (EtOAc:Pet. Ether) to give the desired product.

IR (NaCl, neat) ν: 3313.4, 2980.6, 2938.2, 2879.4, 1743.9, 1694.2, 1681.0, 1661.7, 1651.1, 1547.2, 1453.8, 1372.1, 1249.1, 1164.5 cm$^{-1}$. $^1$H NMR (300 MHz, CDCl$_3$) δ ppm: 8.07 (dd, J=6.0 Hz, 3.3 Hz, 1H), 7.72 (dd, J=8.0 Hz, 3.3 Hz, 2H), 7.60, (dd, J=5.4 Hz, 3.6 Hz, 1H), 7.00 (d, J=7.8 Hz, 1H), 6.94 (t, J=5.1 Hz, 1H), 5.38 (d, J=6.0 Hz, 1H), 4.74 (q, J=7.5 Hz, 1H), 4.46 (quint., J=7.2 Hz, 1H), 4.42-4.41 (m, 1H), 3.59 (s, 3H), 3.45 (ddd, J=15.3 Hz, 102 Hz, 5.1 Hz, 1H), 3.29 (quint, J=6.6 Hz, 1H, 3.16 (quint, J=6.6 Hz, 1H), 3.13 (dt, J=10.2 Hz, 5.1 Hz, 1H), 1.49 (d, J=6.0 Hz, 3H), 1.44 (s, 9H), 1.37 (dd, J=6.9 Hz, 3.0 Hz, 6H). $^{13}$C NMR (75 MHz, CDCl$_3$) δ ppm: 172.6, 172.1, 171.6, 155.7, 148.0, 133.5, 133.0, 131.6, 130.8, 123.8, 80.3, 55.8, 52.2, 48.9, 45.8, 38.6, 28.2, 27.9, 26.5, 21.9, 18.0, 16.5. HRMS (EI) m/z calcd for C$_{25}$H$_{39}$N$_5$O$_{10}$S—601.2418, Found—624.2315 [M+Na]$^+$ (100%).

Example 4C

General Procedure for N-Alkylation of Alkyl Bromides Using K$_2$CO$_3$

A suspension of K$_2$CO$_3$ (3.8 eq.) and a peptidic amine (3 eq.) in acetonitrile (0.15 M in the amine) is stirred for 25 minutes under reflux conditions followed by addition of the alkyl bromide (1 eq.) and is stirred further at 50° C., unto TLC shows complete consumption of the starting peptidic amine (~1-2 days). The reaction mixture is filtered through celite, is concentrated under vacuum and is purified by silica gel flash column chromatography using hexane-EtOAc to furnish the desired N-alkylated compound.

Example 4D

Synthesis of N-Ns-N,N'-Alkylated Peptide

Step I: Synthesis of N-Ns-N-Alkyl Methyl Alaninate

General Procedure for Synthesis of N-Ns-N-(4-bromo-butyl)-Ala-OR

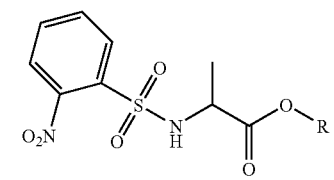

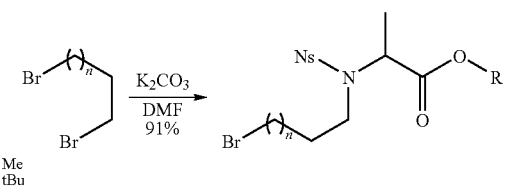

R = Me
 = tBu

To a solution of the N-nosyl protected alkyl alaninate (1 equivalent) in dry DMF (0.2 M) is added K$_2$CO$_3$ (2 equivalents) and 1,3-dibromopropane or 1,4-dibromobutane (4 equivalents) with stirring at 25° C. The mixture was monitored for progress by TLC (developing system ethyl acetate/hexanes: 1:1) until complete consumption of the N-nosyl sulfonamide protected alkyl alaninate (9 h). After completion of the reaction, the mixture was diluted with water and thoroughly washed with ether. The combined organic extracts were dried over Na$_2$SO$_4$ and concentrated in vacuum to give a residue, which was purified by silica gel column chromatography (EtOAc:hexanes—1:6) to yield the desired product in >90% yield.

The following products were synthesized using the above processes.

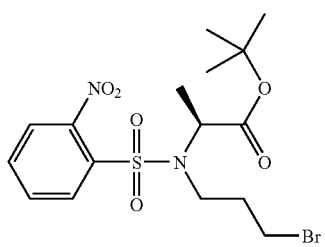 [SMILES: C[C@@H](C(=O)OC(C)(C)C)N(CCCBr)S(=O)(=O)c1ccccc1[N+](=O)[O-]]

Yellow solid: m.p. 40-42° C. $^1$H NMR (300 MHz, CDCl$_3$) δ ppm: 1.34 (s, 9H), 1.51 (d, J=7.5 Hz, 3H), 2.12-2.39 (m, 2H), 3.28-3.65 (m, 3H), 3.54-3.65 (m, 1H), 4.67 (q, J=7.5 Hz, 1H), 7.57-7.62 (m, 1H), 7.66-7.72 (m, 2H), 8.05-8.08 (m, 1H). $^{13}$C NMR (75 MHz, CDCl$_3$) δ ppm 16.9, 27.7, 30.5, 33.7, 45.0, 56.8, 82.2, 124.0, 131.1, 131.5, 133.5, 170.14. HRMS (EI) m/z calculated for [C$_{16}$H$_{23}$BrN$_2$O$_6$S+Na]—473.0358 found—473.0345, 475.0318 [M+Na]$^+$. IR (neat) v: 2979 (C—H), 1732 (C=O), 1370 (S=O), 1149 (C—O) cm$^{-1}$.

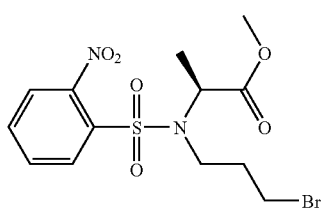 [SMILES: COC(=O)[C@H](C)N(CCCBr)S(=O)(=O)c1ccccc1[N+](=O)[O-]]

Yellow oil. $^1$H NMR (300 MHz, CDCl$_3$) δ ppm: 1.55 (d, J=7.2 Hz, 3H), 2.10-2.39 (m, 2H), 3.33-3.45 (m, 3H), 3.52-3.63 (m, 1H), 3.63 (s, 3H), 4.8 (q, J=7.2 Hz, 1H), 7.59-7.68 (m, 1H), 7.68-7.73 (m, 2H), 8.06-8.09 (m, 1H). $^{13}$C NMR (75 MHz, CDCl$_3$) δ ppm: 16.6 (CH$_3$), 30.4 (CH$_2$—CH$_2$—CH$_2$—Br), 33.4 (CH$_2$—Br), 44.9 (N—CH$_2$), 52.44 (C, 56.17 (OCH$_3$), 124, 131.1, 131.6, 133.6 (Ar), 171.7 (C=O). HRMS (EI) m/z calcd for [C$_{13}$H$_{17}$BrN$_2$O$_6$SNa]: 430.9888 found: 430.9888, 432.9882 [M+Na]$^+$ (100%), 351.0580 (35%). IR (v, cm$^{-1}$) neat, CH$_2$Cl$_2$: 2953 (C—H), 1742 (C=O), 1544 (N—O), 1373 (S=O), 1154 (C—O).

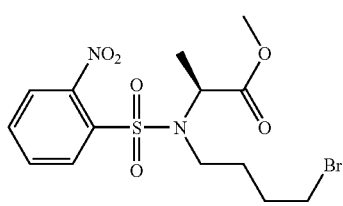 [SMILES: COC(=O)[C@H](C)N(CCCCBr)S(=O)(=O)c1ccccc1[N+](=O)[O-]]

Yellow oil (92% yield). TLC (EtOAc:Hexanes—1:1). $^1$H NMR (300 MHz, CDCl$_3$) δ ppm: 8.07 (dd, J=4.8 Hz, 2.1 Hz, 1H), 7.71 (t, J=6.0 Hz, 2H), 7.63-7.58 (m, 1H), 4.77 (q, J=7.5 Hz, 1H), 3.61 (s, 3H), 3.49 (ddd, J=15 Hz, 10.2 Hz, 5.1 Hz, 1H), 3.38 (t, J=4.8 Hz, 2H), 3.16 (ddd, 15 Hz, 9.6 Hz, 5.7 Hz, 1H), 1.81-1.40 (m, 4H), 1.54 (d, J=7.5 Hz, 3H). $^{13}$C NMR (75 MHz, CDCl$_3$) δ ppm: 16.6, 29.8, 31.3, 32.8, 45.3, 52.3, 55.8, 124, 130.8, 131.5, 133.6, 171.6.

Step II: Synthesis of N-Ns-N,N'-Alkylated Peptide

The procedure of Garnder, et al. may be used (R. Gardner, R. Kinkade, C. Wang, and Phanstiel, *J. Org. Chem.*, 2004, 69 (10), 3530-3537). Similarly, the corresponding butyl bromide can be used for synthesizing the N-butyl product (the following prophetic example).

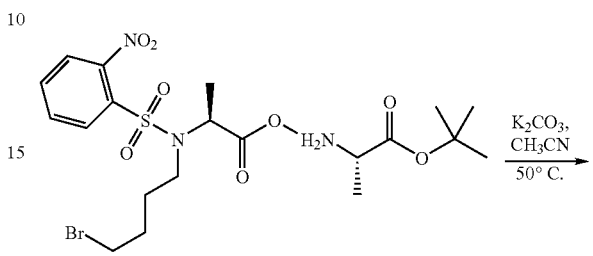

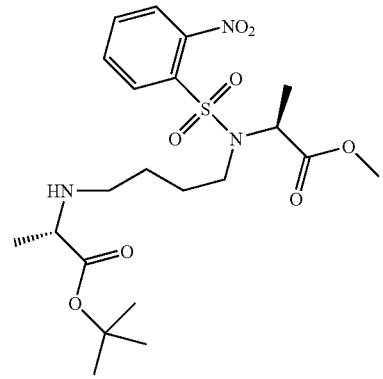

To a suspension of K$_2$CO$_3$ (3.3 equivalents) in dry acetonitrile (~0.5 M in amine) is added $^t$butyl alaninate (2 equivalents), N-(3-bromo propyl), N-Nosyl methyl alaninate (1 equivalent; prepared as in Step I above) and the mixture is stirred at 50° C. The reaction mixture is monitored for progress by TLC (EtOAc:hexanes) and additional portions of $^t$butyl alaninate (1 equivalent) and K$_2$CO$_3$ (0.5 equivalent) are added as required. The reaction is continued until complete consumption of the starting material. Then the reaction mixture is filtered through celite and the filtrate is concentrated to give a residue which is dissolved in diethyl ether (10 mL) and extracted with saturated citric acid (2 mL). The pH of the aqueous portion is adjusted to about 9 by adding NaHCO$_3$ and the aqueous part is extracted with EtOAC. The organic extract is dried over Na$_2$SO$_4$ and concentrated under vacuum to obtain a crude residue which is purified by silica gel flash column chromatography (EtOAc:hexanes) to give the desired product.

Example 5

Intermolecular N-Alkylation of N-Nosyl Peptides with Alcohols

Example 5A

Synthesis of Boc-Ala-Ala-NH—(CH$_2$)$_4$—N(Ns)-Ala-OMe

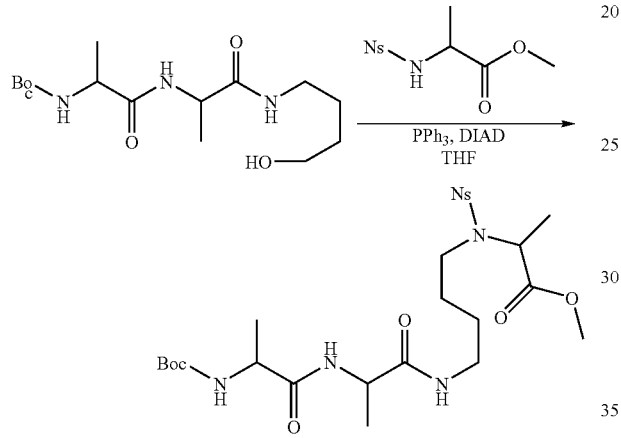

To a cold (−15° C.) vigorously stirring solution of Ns-Ala-OMe (50 mg, 0.17 mmol), Boc-Ala-Ala-NH—(CH$_2$)$_4$—OH (57 mg, 0.17 mmol) and PPh$_3$ (68 mg, 0.26 mmol) in dry THF (1.5 mL) was added DIAD (53 mg, 0.26 mmol) slowly dropwise. After 7 h another portion of PPh$_3$ (68 mg, 0.26 mmol) and DIAD (52 mg, 0.26 mmol) was added and stirred for further 10 h, when TLC (MeOH:DCM) indicated complete consumption of the starting material. The mixture was concentrated under vacuum and the resulting residue was diluted with EtOAc (15 mL), washed with water (2 mL), dried over Na$_2$SO$_4$ and concentrated under vacuum to give a crude residue which was purified by silica gel flash column chromatography (EtOAc:Hexanes—3:1) to give the desired product as a viscous oil in good yields (71 mg, 76%). TLC (MeOH:DCM—1:9—R$_f$=0.5).

IR (NaCl, neat) ν: 3313.4, 2980.6, 2938.2, 2879.4, 1743.9, 1694.2, 1681.0, 1661.7, 1651.1, 1547.2, 1453.8, 1372.1, 1249.1, 1164.5 cm$^{-1}$. $^1$H NMR (300 MHz, CDCl$_3$) δ ppm: 8.07 (dd, J=6.0 Hz, 3.3 Hz, 1H), 7.72 (dd, J=8.0 Hz, 3.3 Hz, 2H), 7.60, (dd, J=5.4 Hz, 3.6 Hz, 1H), 7.00 (d, J=7.8 Hz, 1H), 6.94 (t, J=5.1 Hz, 1H), 5.38 (d, J=6.0 Hz, 1H), 4.74 (q, J=7.5 Hz, 1H), 4.46 (quint., J=7.2 Hz, 1H), 4.42-4.41 (m, 1H), 3.59 (s, 3H), 3.45 (ddd, J=15.3 Hz, 102 Hz, 5.1 Hz, 1H), 3.29 (quint, J=6.6 Hz, 1H, 3.16 (quint, J=6.6 Hz, 1H), 3.13 (dt, J=10.2 Hz, 5.1 Hz, 1H), 1.49 (d, J=6.0 Hz, 3H), 1.44 (s, 9H), 1.37 (dd, J=6.9 Hz, 3.0 Hz, 6H). $^{13}$C NMR (75 MHz, CDCl$_3$) δ ppm: 172.6, 172.1, 171.6, 155.7, 148.0, 133.5, 133.0, 131.6, 130.8, 123.8, 80.3, 55.8, 52.2, 48.9, 45.8, 38.6, 28.2, 27.9, 26.5, 21.9, 18.0, 16.5. HRMS (EI) m/z calcd for O$_{25}$H$_{39}$N$_5$O$_{10}$S—601.2418, Found—624.2315 [M+Na]$^+$ (100%).

Example 6

Reductive Amination

Example 6a

Synthesis of Compound A

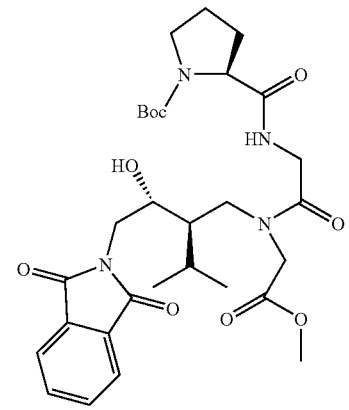

Scheme I:

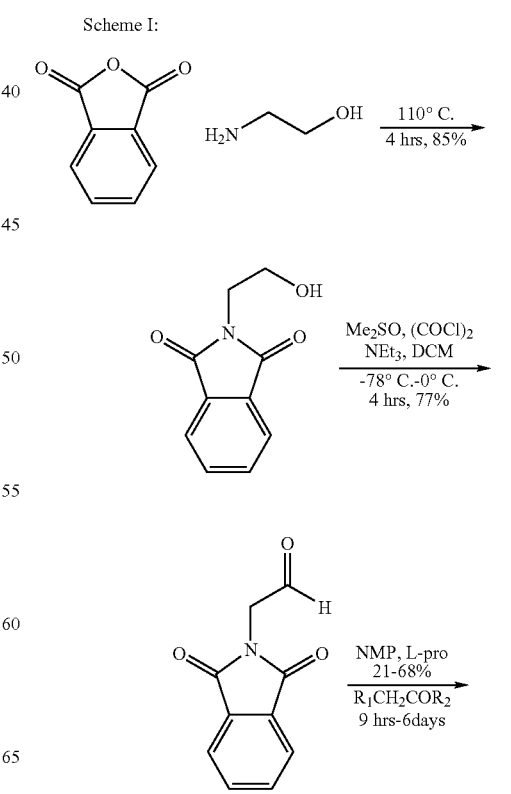

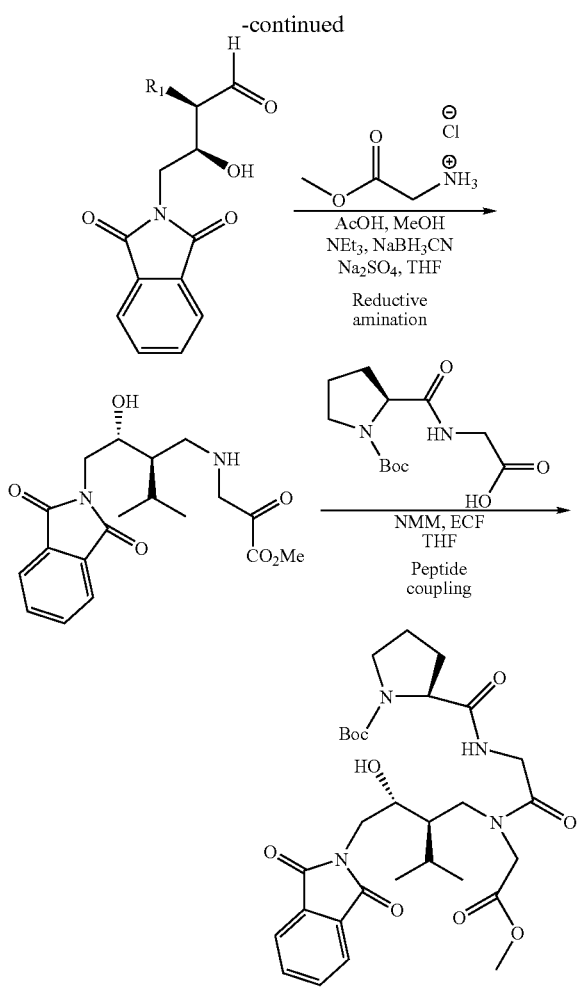

Step I: Synthesis of N-Pthalimido-N-Ethyl-Alcohol

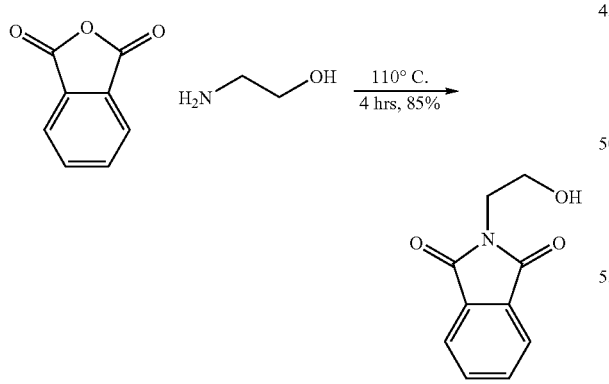

The literature procedure was followed: E. Kolomiets, E. Buhler, S. J. Candau, and J.-M. Lehn, *Macromolecules*, 2006, 39, 1173-1181.

A solution of phthalic anhydride (14.81 g, 100 mmol) in ethanolamine (6.04 mL, 100 mmol) was heated to 110° C. and stirred for 4 hrs. The reaction mixture was to 25° C. and hot water (70° C.) was added which resulted in slow formation of a white precipitate, which was filtered through sintered funnel. The resulting precipitate dried under high vacuum through a $CaCl_2$/KOH tower. The resulting dry residue was purified by silica gel flash column chromatography (EtOAc: Hexanes—1:6) to give the desired product in good yields (16.23 g, 85%) as white solid. (m.p. 126-128° C.). TLC (Hexane:EtOAc 1:3, $R_f$=0.41).

$^1$H NMR (300 MHz, $CDCl_3$) δ ppm: 7.82-7.87 (m, 2H), 7.70-7.74 (m, 2H), 3.88-3.91 (m, 2H), 2.36 (br, 1H). $^{13}$C NMR (75 MHz, $CDCl_3$) δ ppm: 40.8, 61.1, 134.1, 131.9, 123.3, 168.8.

Step II: Synthesis of N-Pthalimido-N-Acetaldehyde

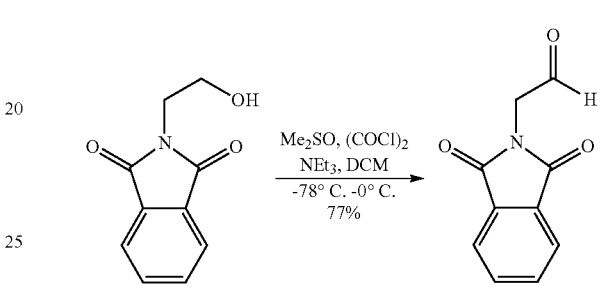

A solution of Oxalyl chloride (3.6 mL, 41.2 mmol) in dry dichloromethane (130 mL) was cooled to −78° C. and stirred for 20 minutes then di methyl sulfoxide (5.84 mL, 82.4 mmol) was added and stirred for further 30 min. To this was added a solution of N-(2-hydroxyethyl) phthalimide (3.95 g, 20.6 mmol) in a mixture of DCM:DMSO (20 mL:3 mL), while maintaining the temperature at −78° C. After 40 min of stirring, $NEt_3$ (11.4 mL, 82.4 mmol) was added and the reaction mixture was allowed to warm 0° C. and stirred for further 4 h. The mixture was quenched with water, diluted with ethyl acetate (50 mL) and washed with distilled water (3×20 mL). The organic layer was dried over $Na_2SO_4$ and concentrated in vacuum to give a residue which was purified by silica gel flash column chromatography (EtOAc:Hexanes—1:6) to yield the desired product in yields (3.02 g, 77%) as a white solid (m.p. 110-112° C.). TLC (EtOAc:hexanes—1:1, $R_f$=0.3).

$^1$H NMR (300 MHz, $CDCl_3$) δ ppm: 9.66 (s, 1H), 7.88-7.91 (m, 2H), 7.76-7.79 (m, 2H), 4.57 (s, 2H). $^{13}$C NMR (75 MHz, $CDCl_3$) δ ppm: 193.4, 167.4, 134.1, 131.9, 123.6, 55.3.

Step III: Synthesis of the Cross-Aldol Product with Isovaleraldehyde

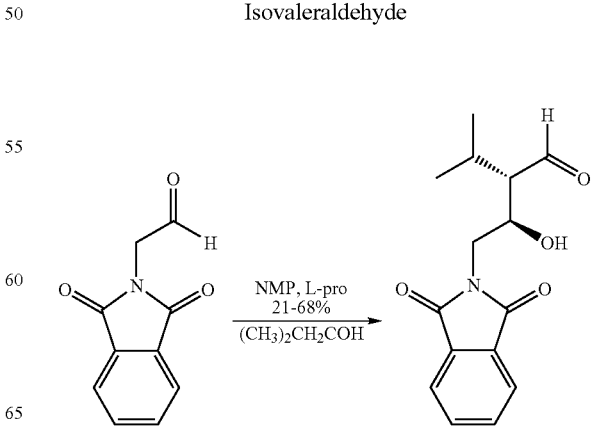

The general procedure that was followed for the synthesis of cross-aldol products was as described in: *Org. Lett.* 2004, 6, 3541-3544. Herein, to a mixture of phthalimidoacetaldehyde (1 eqivalent), and the carbonyl compound (isovaleraldehyde) (10 eqivalents) in NMP (2 M) is added L-proline (0.3 eqivalents)) at 0° C. and the mixture is stirred at 0-4° C. The reaction mixture is monitored for progress by TLC (EtOAc:hexanes) until complete consumption of the phthalimidoacetaldehyde, after which, EtOAc is added and the organic mixture is washed with saturated aqueous $NH_4Cl$, dried over $Na_2SO_4$ and concentrated in vacuum to give a residue which was purified by silica gel flash column chromatography (EtOAc in Hexanes) to yield the desired product. The spectral data match that reported for compound 6a in the Supporting Information of Thayumanavan, et al., *Org. Lett.* 2004, 6, 3541-3544.

Step IV: Synthesis of Reductive Amination Product

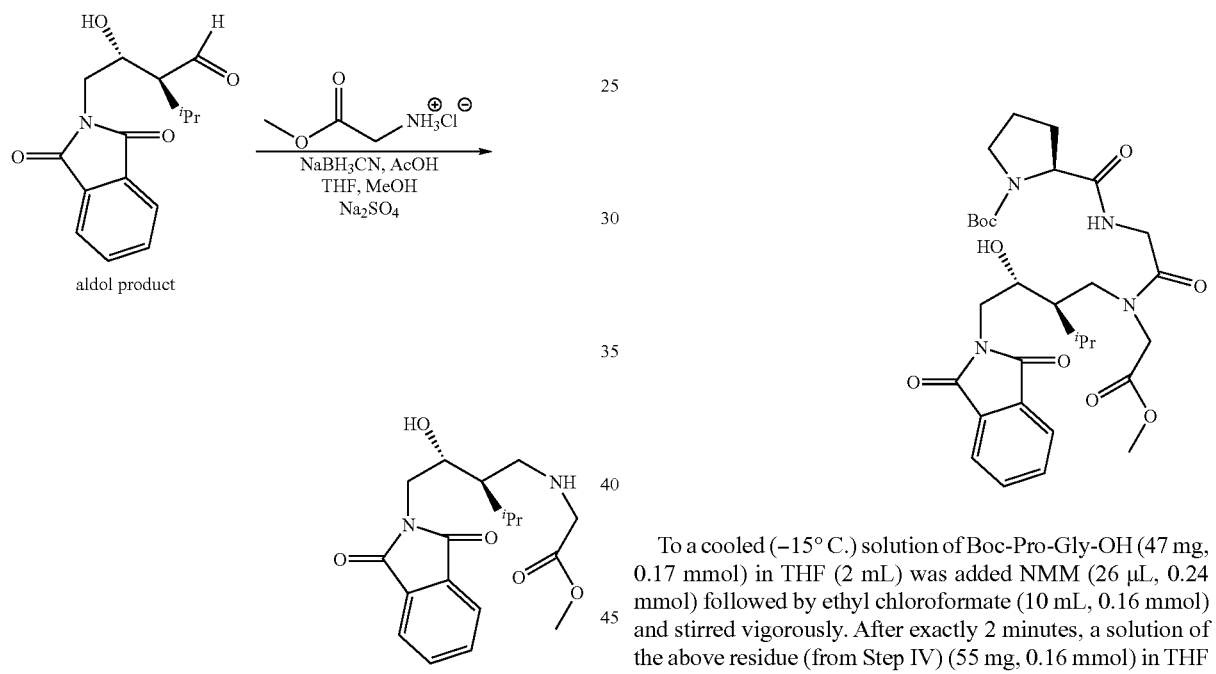

To a mixture of methyl glycinate hydrochloride (37 mg, 0.3 mmol) and $Na_2SO_4$ (211 mg, 1.49 mmol) under $N_2$ atmosphere was added a solution of the N-pthalimido aldol product of Step III (82 mg, 0.3 mmol) in MeOH (1 mL) followed by TEA (41 μL, 0.29 mmol) and stirred for 15 min. Then a solution of AcOH (17 μL, 0.29 mmol) in MeOH (0.5 mL) was added followed by a solution of $NaBH_3CN$ (21 mg, 0.33 mmol) in a mixture of MeOH:THF (1 mL:mL) and the mixture was stirred at 25° C. overnight. The mixture was quenched with saturated solution of $NaHCO_3$ and the solvents were evaporated under reduced pressure to yield a residue which was dissolved in EtOAc. The organic layer was washed with saturated solution of $NaHCO_3$, dried over $Na_2SO_4$, and concentrated under vacuum to give the desired product as the major component as a thick brown oil, which was directly taken up for further reaction. EI HRMS (m/z)—Calculated for $C_{18}H_{25}N_2O_5$—$[M+H]^+$=349.1763, Found=349.1732; Calculated for —$C_{18}H_{24}N_2NaO_5$ $[M+Na]^+$=371.1583, Found=371.1570 (100%); Calculated for —$C_{18}H_{25}N_2NaO_5$—$[M+Na+H]^+$=372.1661, Found=372.1596; Calculated for $C_{18}H_{24}KN_2O_5$—$[M+K]^+$= 387.1322, Found=387.1680.

Step V: Synthesis of Compound A

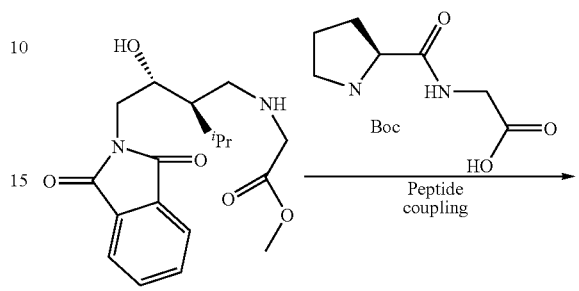

To a cooled (−15° C.) solution of Boc-Pro-Gly-OH (47 mg, 0.17 mmol) in THF (2 mL) was added NMM (26 μL, 0.24 mmol) followed by ethyl chloroformate (10 mL, 0.16 mmol) and stirred vigorously. After exactly 2 minutes, a solution of the above residue (from Step IV) (55 mg, 0.16 mmol) in THF (1 mL) was added along with NMM (43 μL, 0.39 mmol) and stirred for 15 minutes. The mixture was allowed to warm to room temperature and stirred until TLC (EtOAc) indicated the complete consumption of the starting acid (6 h). The solvents were removed under vacuum and the residue was diluted with EtOAc and washed with brine, water, saturated solution of citric acid and saturated $NaHCO_3$ solutions and the organic layer was concentrated under vacuum to yield a residue. Purification by silica gel flash column chromatography (Hexanes:EtOAc—2:3) gave the desired peptide as an oil (53 mg, 55.6%). TLC (EtOAc—$R_f$=0.47) along with traces of an inseparable highly polar compound.

EI HRMS (m/z)—Calculated for—$C_{30}H_{42}N_4NaO_9$ $[M+Na]^+$=625.2849, Found=625.2849 (100%); Calculated for —$C_{30}H_{43}N_4NaO_9[M+Na+H]^+$=626.2928, Found=626.2882; Calculated for —$C_{30}H_{42}KN_4O_9[M+K]^+$ =641.2589, Found=641.2680; Calculated for —$[M+2H-Boc]^+$=503.2505, Found=503.2493; Calculate for —$[M+2H+Na+-Boc]^+$=522.2091, Found=522.2192. IR (NaCl, neat) $CH_2Cl_2$ v: 3335, 2956, 1739, 1710, 1681 $cm^{-1}$.

Example 7

Macrolactamization

Example 7A

General Protocol for Macrolactamization

A 0.05 M solution of the TFA salt of the amino peptidic acid (1 eq.) in DMF is cooled to 0° C. and the HOBT (1.5 eq.) is added and stirred for about 30 min. EDC (1.5 eq.) is added followed by DIPEA (3 eq.) and the mixture is stirred at room temperature until complete disappearance of the spot corresponding to the starting amino peptidic acid from the reaction mixture, on TLC (~36 h). The solvent is removed under vacuum and the resulting residue is diluted with EtOAc and is washed with brine, water, 1 N HCl (or saturated citric acid), saturated NaHCO$_3$. The combined organic extracts are dried (Na$_2$SO$_4$) and are concentrated under vacuum. The resulting residue is purified by silica gel flash column chromatography using hexanes:EtOAc to obtain the desired cyclic lactam.

Example 7B

Synthesis of Ns-[N-Ala-Ala-Ala-NH—(CH$_2$)$_4$]$_{cyclo}$

Step I: Synthesis of N-Boc, N'—Ns Carboxylic Acid

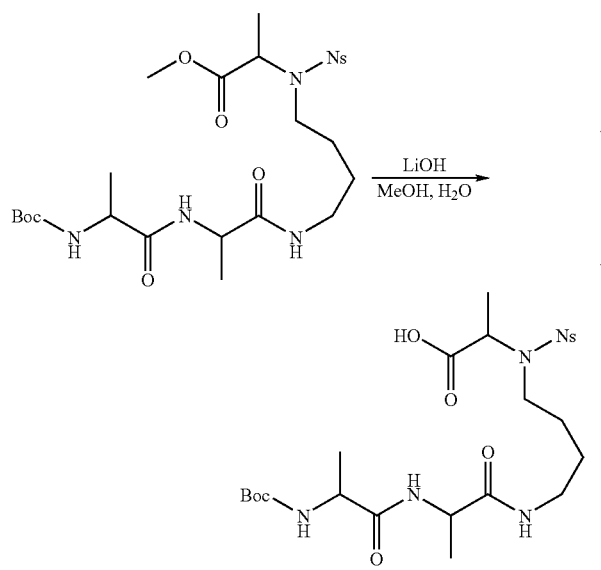

To a solution of LiOH (6.8 mg, 0.16 mmol) in a mixture of solvents MeOH: H$_2$O (1.5 mL: 0.5 mL) was added the N-Boc-N'-Ns-ester (65 mg, 0.11 mmol) from Example 5A and stirred for 4 hours at r.t. The solution was acidified to pH 2-3 with saturated aqueous solution of citric acid and the mixture was extracted with EtOAc (3×20 mL). The organic layer was dried over Na$_2$SO$_4$ and concentrated under vacuum to give the desired product Boc-Ala-Ala-OH as a highly viscous and hygroscopic oil in greater quantitative yields (79 mg). The product was taken for further reactions directly without any purification. TLC—MeOH:DCM—1:9—R$_f$=0.44.

Step II: Synthesis of TFA Salt of N'-Ns-Amino Acid

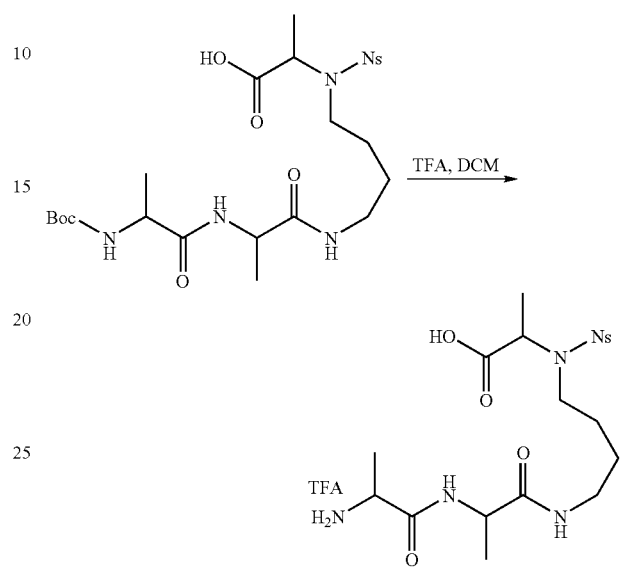

To an ice cold solution of the B-Boc-N'-Ns-ester (60 mg, 0.104 mmol) in dry DCM (1.8 mL) was added TFA (0.2 mL) and stirred for 3 h. The solvent and reagents were removed under vacuum and the resulting product was taken directly for synthesis in the next step. TLC—MeOH:DCM—1:4—R$_f$=0.44.

Step III: Synthesis of Ns-[N-Ala-Ala-Ala-NH-Butyl]$_{cyclo}$

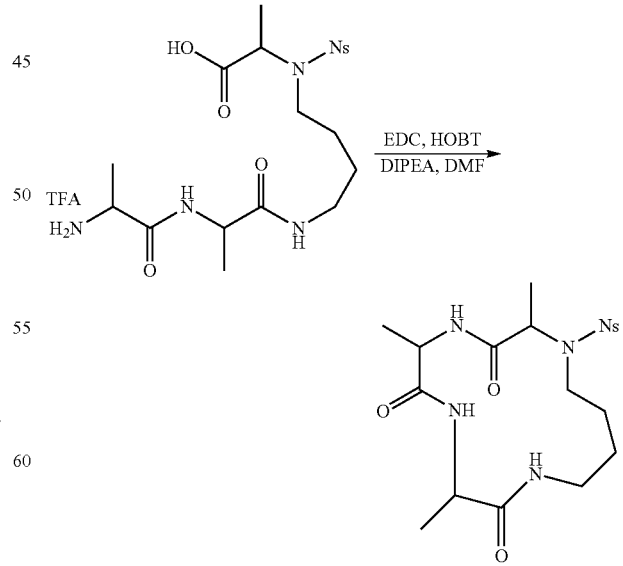

To a vigorously stirring cold (−15° C.) solution of the TFA salt of the N'-Ns-amino acid (50 mg, 0.08 mmol) in dry DMF (40 mL) was added EDC (80 mg, 0.41 mmol), HOBT (56 mg, 0.41 mmol) and DIPEA (87 μL, 0.5 mmol). After 30 minutes, the mixture was warmed to r.t. and stirred for a further 44 h. The mixture was concentrated under vacuum to remove DMF and resulting residue was diluted with EtOAc (10 mL) and washed with brine (5 mL), 5% HCl (5 mL) and saturated solution of NaHCO$_3$ (5 mL). The organic layer was dried over Na$_2$SO$_4$ and concentrated under vacuum to give a residue, which was purified by silica gel flash column chromatography (MeOH:DCM—1:19) to give the desired cyclized product in good yields (30 mg, 77%). TLC—MeOH:DCM—R$_f$=0.53. HRMS (EI) m/z calculated for C$_{19}$H$_{27}$N$_5$NaO$_7$S—492.1529, Found—492.1521 [M+Na]$^+$ (100%), C$_{19}$H$_{28}$N$_5$NaO$_7$S—493.1607, Found—493.1595.

EQUIVALENTS

While certain embodiments have been illustrated and described, it should be understood that changes and modifications can be made therein in accordance with ordinary skill in the art without departing from the technology in its broader aspects as defined in the following claims.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

---

What is claimed is:

1. A compound of Formula I

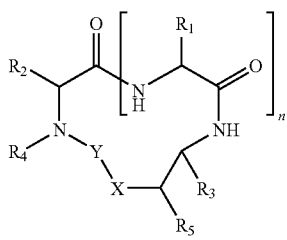

(I)

wherein

X is —$CR_aR_b$—;

Y is —$CR_cR_d$—;

$R_a$, $R_b$, $R_c$, and Rd are independently —H or a substituted or unsubstituted alkyl or aralkyl group;

$R_1$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl, or heteroaralkyl group; or, $R_1$ together with the carbon to which it is attached and the adjacent nitrogen, forms a substituted or unsubstituted pyrrolidine, oxazolidine, thiazolidine, imidazolidine, or piperidine ring;

$R_2$ and $R_3$ are independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group; or $R_2$ and $R_4$ together with the atoms to which they are attached form a substituted or unsubstituted pyrrolidine, oxazolidine, thiazolidine, imidazolidine, or piperidine ring;

$R_4$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, —C(O)—$R_1$, or a —C(O)—$CHR_1$—NH—$R_6$ group; or $R_4$ and $R_2$ together with the atoms to which they are attached form a substituted or unsubstituted pyrrolidine, oxazolidine, thiazolidine, imidazolidine, or piperidine ring;

$R_5$ is a —H, a substituted or unsubstituted alkyl, aryl, aralkyl, heteroaryl or a heteroaralkyl group, —$NH_2$, —NH—C(O)—$R_7$, or a —NH—$CHR_1$—C(O)—$R_7$ group;

$R_6$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, —C(O)$R_{10}$, —C(O)O$R_{10}$, —[C(O)—$CHR_1$—NH]$_m$—$R_{10}$, —[C(O)—$CHR_1$—NH]$_m$—C(O)$R_{10}$, or —[C(O)—$CHR_1$—NH]$_m$—C(O)$R_{10}$;

$R_7$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, —$NR_{10}R_{10}$, —$OR_{10}$ or —[NH—$CHR_{10}$—C(O)]$_m$—;

$R_{10}$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group;

m at each occurrence is independently an integer from 1 to 20; and n is an integer from 1 to 20.

2. The compound of claim 1 wherein $R_a$ is a substituted or unsubstituted $C_{1-6}$ alkyl group, $R_c$ is a substituted or unsubstituted $C_{1-6}$ alkyl group, or both $R_a$ and $R_c$ are substituted or unsubstituted $C_{1-6}$ alkyl groups.

3. The compound of claim 1 wherein X is —$CH_2$—, Y is —$CH_2$—, or each of X and Y is —$CH_2$—.

4. The compound of claim 1 wherein $R_1$ and $R_2$ are independently —H, benzyl optionally substituted with one or more OH or halogen, imidazolylmethyl, indolylmethyl, or a $C_{1-6}$ alkyl group optionally substituted with one or more substituents selected from —F, —Cl, —Br, —I, —OH, —O—$PG_1$, —SH, —S—$PG_2$, —$NH_2$, —NH-$PG_3$, —C(O)OH, —C(O)O—$PG_4$, —C(O)$NH_2$, or —NHC(NH)$NH_2$; and wherein $PG_1$ is a hydroxyl protecting group;

$PG_2$ is a thiol protecting group;

$PG_3$ is an amino protecting group; and $PG_4$ is a carboxyl protecting group.

5. The compound of claim 1 wherein $R_2$ and $R_4$ together with the atoms to which they are attached form a substituted or unsubstituted pyrrolidine ring.

6. The compound of claim 1 wherein $R_4$ is a —C(O)—$CHR_1$—NH—$R_6$ group.

7. The compound of claim 1 wherein $R_6$ is —H, —C(O)$R_{10}$, —C(O)O$R_{10}$, —[C(O)—$CHR_1$—NH]$_m$—$R_{10}$, or —[C(O)—$CHR_1$—NH]$_m$—C(O)$R_{10}$.

8. The compound of claim 1 wherein $R_5$ is a —NH—$CHR_1$—C(O)—$R_7$ group.

9. The compound of claim 1 wherein $R_7$ is —$OR_{10}$, —$NR_{10}R_{10}$, or —[NH—$CHR_1$—C(O)]$_m$—.

10. A compound of Formula I

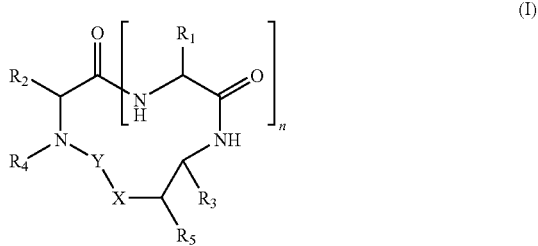

(I)

wherein

X is —$CR_aR_b$—;

Y is —$CR_cR_d$—;

$R_a$, $R_b$, $R_c$, and Rd are independently —H or a substituted or unsubstituted alkyl or aralkyl group;

$R_1$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl, or heteroaralkyl group; or, $R_1$ together with the carbon to which it is attached and the adjacent nitrogen, forms a substituted or unsubstituted pyrrolidine, oxazolidine, thiazolidine, imidazolidine, or piperidine ring;

$R_2$ is —H or a substituted or unsubstituted alkyl, cycloalkyl, cycloalkylalkyl, alkenyl, aryl, aralkyl, heterocyclyl; heterocyclylalkyl, heteroaryl or heteroaralkyl group; or $R_2$ and $R_4$ together with the atoms to which they are attached form a substituted or unsubstituted pyrrolidine, oxazolidine, thiazolidine, imidazolidine, or piperdine ring;

$R_3$ is a substituted or unsubstituted alkyl, cycloalkyl, cycloalkylalkyl, alkenyl, aryl, aralkyl, heterocyclyl, heterocyclylalkyl, heteroaryl or heteroaralkyl group, $R_4$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, —C(O)—$R_1$, or a —C(O)—$CHR_1$—NH—$R_6$ group; or $R_4$ and $R_2$ together with the atoms to which they are attached form a substituted or unsubstituted pyrrolidine, oxazolidine, thiazolidine, imidazolidine, or piperidine ring;

$R_5$ is a —H, a substituted or unsubstituted alkyl, aryl, aralkyl, heteroaryl or a heteroaralkyl group, —$NH_2$, —NH—C(O)—$R_7$, or a —NH—$CHR_1$—C(O)—$R_7$ group;

$R_6$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, —$C(O)R_{10}$, —$C(O)OR_{10}$, —[C(O)—$CHR_1$—NH]$_m$—$R_{10}$, —[C(O)—$CHR_1$—NH]$_m$—$C(O)R_{10}$, or —[C(O)—$CHR_1$—NH]$_m$—$C(O)R_{10}$;

$R_7$ is —H, a substituted or unsubstituted alkyl, cycloalkyl, cycloalkylalkyl, alkenyl, aryl, aralkyl, heterocyclyl, heterocyclylalkyl, heteroaryl or heteroaralkyl group, —$NR_{10}R_{10}$, —$OR_{10}$, or —[NH—CH $R_{10}$—C(O)]$_m$;

$R_{10}$ at each occurrence is independently —H or a substituted or unsubstituted alkyl, cycloalkyl, cycloalkylalkyl, alkenyl, aryl, aralkyl, heterocyclyl, heterocyclylalkyl, heteroaryl or heteroaralkyl group;

m at each occurrence is independently an integer from 1 to 20; and n is an integer from 1 to 20.

11. The compound of claim 1, wherein n is 1, 2, or 3.

12. The compound of claim 3, wherein n is 1, 2, or 3.

13. The compound of claim 10, wherein n is 1, 2, or 3.

* * * * *

UNITED STATES PATENT AND TRADEMARK OFFICE
CERTIFICATE OF CORRECTION

PATENT NO. : 8,563,686 B2
APPLICATION NO. : 12/551101
DATED : October 22, 2013
INVENTOR(S) : Prabhakaran It is certified that error appears in the above-identified patent and that said Letters Patent is hereby corrected as shown below:

On the Title Page

Item (75), under "Inventors", in Column 1, Lines 1-2, delete "IN (US)" and insert -- IN --, therefor.

Item (56), under "OTHER PUBLICATIONS", in Column 1, Line 1, delete "et. al." and insert -- et al. --, therefor.

Item (56), under "OTHER PUBLICATIONS", in Column 1, Lines 5-8, delete "Matsumoto et. al. Novel synthesis of alpha-amino carboxamides and their related compounds via alpha-oxo sulfones starting from 2,2 disulfoxiranes, Bulletin of the Chemical Society of Japan, 77(10), 1897-1903, 2004.*".

Item (56), under "OTHER PUBLICATIONS", in Column 1, Line 10, delete "2004).*" and insert -- 2004.* --, therefor.

On Page 2, Item (56), under "OTHER PUBLICATIONS", in Column 1, Line 8, delete "metrepressor-operator" and insert -- met repressor-operator --, therefor.

On Page 2, Item (56), under "OTHER PUBLICATIONS", in Column 1, Line 38, delete "Relationshops" and insert -- Relationships --, therefor.

On Page 2, Item (56), under "OTHER PUBLICATIONS", in Column 2, Line 17, delete "0-Acyl" and insert -- O-Acyl --, therefor.

In the Specification

In Column 6, Line 39, delete "$R^{42}$" and insert -- $R^{42}$, --, therefor.

Signed and Sealed this
First Day of July, 2014

Michelle K. Lee
*Deputy Director of the United States Patent and Trademark Office*

CERTIFICATE OF CORRECTION (continued)
U.S. Pat. No. 8,563,686 B2

In Column 7, Line 31, delete "methylhiomethyl" and insert -- methylthiomethyl --, therefor.

In Column 8, Line 27, delete "aroyloxyalkyl," and insert -- aryloxyalkyl, --, therefor.

In Column 14, Line 5, delete "pthalimide." and insert -- phthalimide. --, therefor.

In Column 17, Lines 19-20, delete "Fukuyama-Mistsunobu" and insert -- Fukuyama-Mitsunobu --, therefor.

In Column 17, Line 29, delete "Fukuyama-Mistsunobu" and insert -- Fukuyama-Mitsunobu --, therefor.

In Column 17, Line 65, delete "Kl," and insert -- KI, --, therefor.

In Column 18, Line 15, delete "Fukuyama-Mistsunobu" and insert -- Fukuyama-Mitsunobu --, therefor.

In Column 18, Line 39, delete "temperature." and insert -- temperature, --, therefor.

In Column 28, in Table, under "Reference", Line 20, delete "Nol. Biol.," and insert -- Mol. Biol., --, therefor.

In Column 31, Line 46, delete "C12H22N2NaO5:" and insert -- $C_{12}H_{22}N_2NaO_5$: --, therefor.

In Column 35, Line 16, delete "[M-TFA+H]$^+$," and insert -- [M-TFA+H]$^+$. --, therefor.

In Column 35, Line 39, delete "(H-(Ala)$_3$-NH-(CH$_2$)$_4$)-OH)" and insert -- (H-(Ala)$_3$-NH-(CH$_2$)$_4$-OH) --, therefor.

In Column 36, Line 21, delete " $\xrightarrow{\text{(Boc)}_2\text{O}}_{\text{Net}_3,\text{ DCM}}$ " and insert -- $\xrightarrow{\text{(Boc)}_2\text{O}}_{\text{NEt}_3,\text{ DCM}}$ --, therefor.

In Column 38, Line 10, delete "50°C., unto" and insert -- 50°C. until --, therefor.

In Column 41, Line 63, delete "1H," and insert -- 1H), --, therefor.

In Column 42, Line 2, delete "O$_{25}$H$_{39}$N$_5$O$_{10}$S-601.2418," and insert -- $C_{25}H_{39}N_5O_{10}S$-601.2418, --, therefor.

In Column 43, Line 42, delete "N-Pthalimido-N-Ethyl-Alcohol" and insert -- N-Phthalimido-N-Ethyl-Alcohol --, therefor.

In Column 44, Line 6, delete "solid." and insert -- solid --, therefor.

In Column 44, Line 13, delete "N-Pthalimido-N-Acetaldehyde" and insert -- N-Phthalimido-N-Acetaldehyde --, therefor.

In Column 45, Line 4, delete "(1 eqivalent)," and insert -- (1 equivalent), --, therefor.

In Column 45, Line 5, delete "(10 eqivalents)" and insert -- (10 equivalents) --, therefor.

In Column 45, Line 6, delete "eqivalents))" and insert -- equivalents) --, therefor.

In Column 45, Line 51, delete "N-pthalimido" and insert -- N-phthalimido --, therefor.

In the Claims

In Column 56, Line 13, in Claim 1, delete "or –[NH–CH $R_{10}$–C(O)]$_m$–;" and insert -- or –[NH–CHR$_1$–C(O)]$_m$–; --, therefor.

In Column 57, Line 4, in Claim 10, delete "Rd" and insert -- $R_d$ --, therefor.

In Column 57, Line 19, in Claim 10, delete "piperdine ring;" and insert -- piperidine ring; --, therefor.

In Column 57, Lines 22-23, in Claim 10, delete "aralkyl,…………group," and insert the same at Line 21, after "aryl,", as a continuation sub-point.

In Column 58, Line 13, in Claim 10, delete "(O)–CHR$_1$–NH]$_m$–C(O)R$_{10}$;" and insert -- (O)–CHR$_1$–NH]$_m$–C(O)OR$_{10}$; --, therefor.

In Column 58, Line 17, in Claim 10, delete "or –[NH–CH $R_{10}$–C(O)]$_m$–;" and insert -- or –[NH–CHR$_1$–C(O)]$_m$–; --, therefor.

UNITED STATES PATENT AND TRADEMARK OFFICE
CERTIFICATE OF CORRECTION

| | |
|---|---|
| PATENT NO. | : 8,563,686 B2 |
| APPLICATION NO. | : 12/551101 |
| DATED | : October 22, 2013 |
| INVENTOR(S) | : Prabhakaran |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 632 days.

Signed and Sealed this
Seventeenth Day of February, 2015

Michelle K. Lee
*Deputy Director of the United States Patent and Trademark Office*

SEQUENCE LISTING

```
<160> NUMBER OF SEQ ID NOS: 12

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Phe Trp Lys Thr
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp

<400> SEQUENCE: 2

Phe Trp Lys Thr
1
```

```
<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      cyclic peptide
<220> FEATURE:
<221> NAME/KEY: MOD_RES
<222> LOCATION: (1)..(1)
<223> OTHER INFORMATION: D-Phe
<220> FEATURE:
<221> NAME/KEY: MOD_RES
<222> LOCATION: (4)..(4)
<223> OTHER INFORMATION: Ornithine
<220> FEATURE:
<221> NAME/KEY: MOD_RES
<222> LOCATION: (6)..(6)
<223> OTHER INFORMATION: D-Phe
<220> FEATURE:
<221> NAME/KEY: MOD_RES
<222> LOCATION: (9)..(9)
<223> OTHER INFORMATION: Ornithine

<400> SEQUENCE: 3

Phe Pro Val Xaa Leu Phe Pro Val Xaa Leu
1               5                   10

<210> SEQ ID NO 4
<211> LENGTH: 4
<212> TYPE: PRT
<213> ORGANISM: Plasmodium falciparum

<400> SEQUENCE: 4

Asn Pro Asn Ala
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

His Phe Arg Trp
1

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: D-Arg

<400> SEQUENCE: 6

Tyr Phe Gln Asn Cys Pro Arg Gly
1               5

<210> SEQ ID NO 7
<211> LENGTH: 7
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Arg or Gln

<400> SEQUENCE: 7

Gly Pro Gly Xaa Pro Gly Gln
1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Phe Trp Lys Thr Ala
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Phe Trp Lys Ala Ala
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Cys Tyr Phe Gln Asn Cys Pro Arg Gly
1               5

<210> SEQ ID NO 11
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: D-Trp

<400> SEQUENCE: 11

Tyr Trp Lys Thr
1

<210> SEQ ID NO 12
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (2)..(2)
<223> OTHER INFORMATION: D-Trp

<400> SEQUENCE: 12

Tyr Trp Lys Val
1
```